US009399065B2

(12) United States Patent
Pohl et al.

(10) Patent No.: US 9,399,065 B2
(45) Date of Patent: Jul. 26, 2016

(54) MAGNESIUM COMPOSITIONS FOR MODULATING THE PHARMACOKINETICS AND INJECTION SITE PAIN OF INSULIN

(71) Applicant: Biodel, Inc., Danbury, CT (US)

(72) Inventors: Roderike Pohl, Sherman, CT (US);
Robert Hauser, Columbia, MD (US);
Errol De Souza, Cambridge, MA (US);
Ming Li, Yorktown Heights, NY (US);
Bryan R. Wilson, Brewster, NY (US)

(73) Assignee: Biodel Inc., Danbury, CT (US)

( * ) Notice: Subject to any disclaimer, the term of this patent is extended or adjusted under 35 U.S.C. 154(b) by 0 days.

(21) Appl. No.: 14/275,749

(22) Filed: May 12, 2014

(65) Prior Publication Data
US 2014/0357554 A1 Dec. 4, 2014

Related U.S. Application Data

(63) Continuation-in-part of application No. 13/826,806, filed on Mar. 14, 2013.

(60) Provisional application No. 61/822,255, filed on May 10, 2013, provisional application No. 61/704,066, filed on Sep. 21, 2012, provisional application No. 61/624,844, filed on Apr. 16, 2012.

(51) Int. Cl.
| | | |
|---|---|---|
| *A61K 47/02* | (2006.01) | |
| *A61K 38/28* | (2006.01) | |
| *A61K 9/00* | (2006.01) | |
| *A61K 47/12* | (2006.01) | |
| *A61K 47/18* | (2006.01) | |

(52) U.S. Cl.
CPC ............... *A61K 47/02* (2013.01); *A61K 9/0019* (2013.01); *A61K 38/28* (2013.01); *A61K 47/12* (2013.01); *A61K 47/183* (2013.01)

(58) Field of Classification Search
USPC .......................................................... 514/6.4
See application file for complete search history.

(56) References Cited

U.S. PATENT DOCUMENTS

| | | | |
|---|---|---|---|
| 4,196,196 | A | 4/1980 | Tiholiz |
| 5,070,186 | A | 12/1991 | Joergensen |
| 7,279,457 | B2 | 10/2007 | Pohl |
| 2007/0235365 | A1 | 10/2007 | Pohl |
| 2008/0085298 | A1 | 4/2008 | Pohl |
| 2008/0090753 | A1 | 4/2008 | Pohl |
| 2008/0096800 | A1 | 4/2008 | Pohl |
| 2009/0280532 | A1 | 11/2009 | Gorfien |
| 2009/0304665 | A1 | 12/2009 | Frost |
| 2010/0151435 | A1 | 6/2010 | Thatte |

FOREIGN PATENT DOCUMENTS

| | | |
|---|---|---|
| EP | 1044015 | 3/2005 |
| WO | 2009134380 | 11/2009 |
| WO | 2012006283 | 1/2012 |

OTHER PUBLICATIONS

Shoaybi et al. (The effect of Magnesium sulfate on reducing Propofol injection pain in elective surgeries; Tehran University Medical Journal; vol. 64(2), May 2007: 30-34).*
Betenson, et al, "Insulin analogs for the treatment of diabetes mellitus: therapeutic applications of protein engineering", Ann. NY Acad. Sci., 1243:E40-E54 (2011).
Birnbaum, et al, "Assembly and dissociation of human insulin and LysB28ProB29-insulin hexamers: a comparison study", Pharm Res., 14(1) 25-36 (1997).
Brader, et al., "Characterization of the R-state insulin hexamer and its derivatives. The hexamer is stabilized by heterotropic ligand binding interactions", Biochemistry, 30 (27):6636-45 (1991).
Brzovic, et al., "Structural asymmetry and half-site reactivity in the T to R allosteric transition of the insulin hexamer", Biochemistry, 33(44):13057-69 (1994).
Charkoudian and Franz, "A pro-chelator triggered by hydrogen peroxide inhibits iron-promoted hydroxyl radical fornfalion", J. Am. Chem. Soc., 128(38) 12424-5 (2006).
Chen, et al, "Ascorbate in pharmacologic concentrations selectively generates ascorbate radical and hydrogen peroxide in extracellular fluid in vivo", PNAS, 104 (21)8749-54 (2007).
Dickens, et al., "A prochelator activated by hydrogen peroxide prevents metal-induced amyloid Beta aggregation", Chembiochem., 11(1) 59-62 (2010).
Faa, et al., "Zinc in gastrointestinal and liver disease", Coordination Chemistry Reviews, 252:1257-69 (2008).
Ferrari, et al., "Raman signatures of ligand binding and allosteric conformation change in hexameric insulin", Biopolymers, 62(5):249-60 (2001).
Huus, et al., "Ligand binding and thermostability of different allosteric states of the insulin zinc-hexamer", Biochemistry, 45(12):4014-24 (2006).
Lacy, et al., "Role of xanthine oxidase in hydrogen peroxide production", Free Radic. Biol. Med., 25(6)720-7 (1998).
Niethammer, et al., "A tissue-scale gradient of hydrogen peroxide mediates rapid wound detection in zebrafish", Nature, 459:996-9(2009).
Perez and Franz, "Minding metals: tailoring multifunctional chelating agents for neurodegenerative disease", Dalton Trans., 39(9) 2177-87(2010).

(Continued)

*Primary Examiner* — James H Alstrum Acevedo
*Assistant Examiner* — Tara Martinez
(74) *Attorney, Agent, or Firm* — Pabst Patent Group LLP

(57) ABSTRACT

Compositions and methods for modulating injection site pain associated with rapid acting injectable insulin formulations have been developed for subcutaneous injection. The formulations contain insulin in combination with a zinc chelator such as ethylenediaminetetraacetic acid ("EDTA"), a dissolution/stabilization agent such as citric acid, a magnesium salt, and, optionally, additional excipients. New presentations include rapid acting concentrated insulin formulations and a way to enhance the absorption of commercially available rapid acting analog formulations by mixing them with a vial containing dry powder excipients that accelerate their absorption. Devices for mixing excipient and insulin together at the time of administration, while minimizing residence time of the mixture, are also described.

23 Claims, 18 Drawing Sheets

(56) References Cited

OTHER PUBLICATIONS

Pohl et al, "Ultra-rapid absorption of recombinant human insulin induced by zinc chelation and surface charge masking", J. Diabetes Sci.Technol, 6(4)755-763) (2012).

Shin, et al., "Evaluation of dose effects of magnesium sulfate on rocuronium injection pain and hemodynamic changes by laryngoscopy and endotracheal intubation", Korean J Anesthesiol, 60(5):329-33 (2011).

Steiner, et al., "A novel insulin formulation with a more rapid onset of action", Diabetologia, 51:1602-1606 (2008).

Wei and Guo, "Hydrogen peroxide triggered prochelator activation, subsequent metal chelation, and attenuation of the fenton reaction", Angew Chem. Int. Ed Engl., 46(25) 4722-5 (2007).

Zou, et al., "The molecular mechanism of stabilization of proteins by TMAO and its ability to counteract the effects of urea", J Am Chem Soc.,124(7):1192-202 (2002).

* cited by examiner

Sample Name: BIOD-250, 194-105 12_0730 T-0 AVG

Z-Average (d.nm): 167.1
PdI: 0.238

|  | Size (d.nm): | %Volume: |
|---|---|---|
| Peak 1: | 5.100 | 100.00 |
| Peak 2: | 33.06 | 0.0 |
| Peak 3: | 0.000 | 0.0 |

|  | Size (d.nm): | % Intensity: |
|---|---|---|
| Peak 1: | 6.818 | 60.4 |
| Peak 2: | 186.6 | 36.0 |
| Peak 3: | 39.24 | 3.3 |

Sample Name: BIOD-250 194-105, 12_0730 8d 37C AVG

Z-Average (d.nm): 23.36
PdI: 0.263

|  | Size (d.nm): | % Volume: |
|---|---|---|
| Peak 1: | 3.810 | 67.65 |
| Peak 2: | 15.86 | 32.35 |
| Peak 3: | 0.000 | 0.000 |

|  | Size (d.nm): | % Intensity: |
|---|---|---|
| Peak 1: | 32.89 | 96.3 |
| Peak 2: | 4.525 | 3.5 |
| Peak 3: | 4178 | 0.2 |

MAGNESIUM COMPOSITIONS FOR MODULATING THE PHARMACOKINETICS AND INJECTION SITE PAIN OF INSULIN

CROSS REFERENCE TO RELATED APPLICATIONS

This application claims benefit of U.S. Provisional Application No. 61/822,255 filed May 10, 2013, and U.S. Ser. No. 13/826,806 filed Mar. 14, 2013, which claims priority to U.S. Provisional Application No. 61/704,066, filed Sep. 21, 2012, and 61/624,844, filed Apr. 16, 2012, which are herein incorporated by reference in their entirety.

FIELD OF THE INVENTION

The invention is in the general field of injectable rapid acting insulin formulations with reduced injection site pain.

BACKGROUND OF THE INVENTION

Because patients with Type 1 diabetes produce no insulin, the primary treatment for Type 1 diabetes is daily intensive insulin therapy. The treatment of Type 2 diabetes typically starts with management of diet and exercise. Although helpful in the short-run, treatment through diet and exercise alone is not an effective long-term solution for the vast majority of patients with Type 2 diabetes. When diet and exercise are no longer sufficient, treatment commences with various non-insulin oral medications. These oral medications act by increasing the amount of insulin produced by the pancreas, by increasing the sensitivity of insulin-sensitive cells, by reducing the glucose output of the liver or by some combination of these mechanisms. These treatments are limited in their ability to manage the disease effectively and generally have significant side effects, such as weight gain and hypertension. Because of the limitations of non-insulin treatments, many patients with Type 2 diabetes deteriorate over time and eventually require insulin therapy to support their metabolism. As their insulin resistance progresses, higher and higher doses of insulin are required to lower glucose levels. Concentrated insulin up to U-500 (500 units per ml) is commercially available for these patients, but it is limited to basal use due to a slow absorption profile.

Insulin therapy has been used for more than 80 years to treat diabetes. This therapy usually involves administering several injections of insulin each day. These injections consist of administering a long-acting basal injection one or two times per day and an injection of a fast-acting insulin at meal-time. Although this treatment regimen is accepted as effective, it has limitations. First, patients generally dislike injecting themselves with insulin due to the inconvenience and pain of needles. As a result, patients tend not to comply adequately with the prescribed treatment regimens and are often improperly medicated.

More importantly, even when properly administered, insulin injections do not replicate the natural time-action profile of insulin. In particular, the natural spike of the first-phase insulin release in a person without diabetes results in blood insulin levels rising within several minutes of the entry into the blood of glucose from a meal. By contrast, injected insulin enters the blood slowly, with peak insulin levels occurring within 80 to 100 minutes following the injection of regular human insulin.

One of the key improvements in insulin treatments was the introduction in the 1990s of rapid-acting insulin analogs, such as HUMALOG® (insulin lispro), NOVOLOG® (insulin aspart) and APIDRA® (insulin glulisine). However, even with the rapid-acting insulin analogs, peak insulin levels typically occur within 50 to 70 minutes following the injection. Because the rapid-acting insulin analogs do not adequately mimic the first-phase insulin release, diabetics using insulin therapy continue to have inadequate levels of insulin present at the initiation of a meal and too much insulin present between meals. This lag in insulin delivery can result in hyperglycemia early after meal onset. Furthermore, the excessive insulin between meals may result in an abnormally low level of blood glucose known as hypoglycemia. Hypoglycemia can result in loss of mental acuity, confusion, increased heart rate, hunger, sweating and faintness. At very low glucose levels, hypoglycemia can result in loss of consciousness, coma and even death. According to the American Diabetes Association, or ADA, insulin-using diabetic patients have on average 1.2 serious hypoglycemic events per year, many of which events require hospital emergency room visits by the patients.

The rapidity of insulin action is dependent on how quickly it is absorbed. When regular human insulin is injected subcutaneously at 100 IU/ml, the formulation is primarily composed of hexamers (approximately 36 kDa) which are not readily absorbed due to their size and charge. Located within the hexamer are two zinc atoms that stabilize the molecule. Post injection, a concentration driven dynamic equilibrium occurs in the subcutaneous tissue causing the hexamers to dissociate into dimers (about 12 kDa), then monomers (about 6 kDa). Historically, these regular human insulin formulations require approximately 120 min. to reach maximum plasma concentration levels.

Insulin formulations with a rapid onset of action, such as VIAject®, are described in U.S. Pat. No. 7,279,457, and U.S. Published Applications 2007/0235365, 2008/0085298, 2008/90753, and 2008/0096800, and Steiner, et al., *Diabetologia*, 51:1602-1606 (2008). The rapid acting insulin formulations were designed to create insulin formulations that provide an even more rapid pharmacokinetic profile than insulin analogs, thereby avoiding the patient becoming hyperglycemic in the first hour after injection and hypoglycemic two to four hours later. The rapid onset of VIAJECT® results from the inclusion of two key excipients, a zinc chelator such as disodium EDTA (EDTA) and/or calcium disodium EDTA which rapidly dissociates insulin hexamers into monomers and dimers and a dissolution/stabilization agent such as citric acid which stabilizes the dissociated monomers and dimers prior to being absorbed into the blood (Pohl et al, *J. Diabetes Sci. and Technology*, 2012. 6(4)755-763).

Unfortunately, early clinical trials with this product showed injection site discomfort. Inclusion of calcium, either as calcium chloride and/or the calcium salt of the EDTA, decreased injection site pain, supporting the theory that pain arose due to removal of calcium from the extracellular fluid in the injection site vicinity. However, the addition of calcium altered the pharmacokinetics.

It is an object of this invention to provide compositions of ultra-rapid acting injectable insulin compositions with reduced injection site discomfort. It is also an object of the present invention to provide specific concentrated insulin formulations for treating insulin resistant diabetic which modulate the pharmacokinetics and pharmacodynamics of injectable insulin compositions by increasing the rate of absorption from the site of subcutaneous injection.

SUMMARY OF THE INVENTION

Compositions and methods for modulating the pharmacokinetics and pharmacodynamics of ultra-rapid acting injectable insulin formulations with improved injection site tolerability have been developed. The formulations contain insulin in combination with a zinc chelator such as ethylenediamine tetraacetic acid ("EDTA") preferably as the sodium and/or calcium salt, a dissolution/stabilization agent such as citric acid and/or sodium citrate which binds to the charges on the dissociated insulin monomers and dimers, one or more magnesium compounds, and, optionally, additional excipients.

In one embodiment, the formulation contains recombinant human insulin, sodium EDTA, a dissolution/stabilization agent such as citric acid and/or sodium citrate, and one or more magnesium compounds, such as magnesium EDTA, $Mg(OH)_2$, $MgSO_4$, or combinations thereof. In a particular embodiment, the magnesium compound is $MgSO_4$. The concentration of magnesium compounds is between about 0.1 and 10 mg/ml, preferably from between about 0.1 and 5 mg/ml, more preferably between about 0.1 and 2 mg/ml, most preferably between about 0.2 and 2 mg/ml. In some embodiments, the formulations contain between about 0.2-0.3 mg/ml $Mg(OH)_2$ (e.g., 0.282), about 1.7-2.0 magnesium EDTA (e.g., 1.89), and/or about 0.4-0.5 magnesium sulfate (e.g., 0.481). Stability is enhanced by optimizing preservative such as m-cresol and citrate ion concentration. The concentration of the insulin in the formulation is between 100 and 500 units/mL.

In the preferred embodiment, the formulations are administered via subcutaneous injection.

BRIEF DESCRIPTION OF THE DRAWINGS

FIG. 3, 0-480 minutes) post-dose of the Mg EDTA insulin formulations BIOD 123 and 125 compared to HUMALOG®.

FIG. 7B is BIOD-548 containing calcium EDTA, and 7C is same formulation with disodium EDTA.

DETAILED DESCRIPTION OF THE INVENTION

Figure 1:
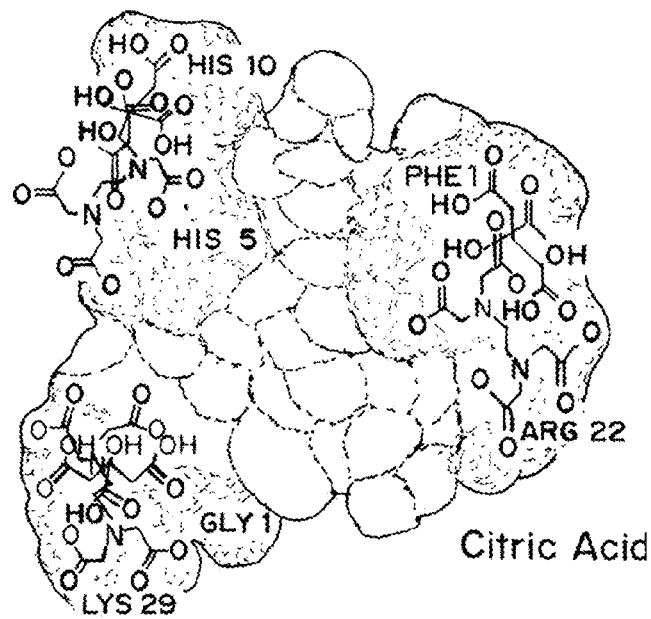
FIG. 1 is a three dimensional schematic of insulin showing exposed surface charges and overlaid with molecules ("dissolution and chelating agents") of appropriate size to mask the charge.

The insulin formulations disclosed herein are administered immediately prior to a meal or at the end of a meal. The formulations are designed to be absorbed into the blood faster than the currently marketed rapid-acting insulin or insulin analogs. One of the key features of the formulation of insulin is that a zinc chelator is included which dissociates, or separates, the hexameric form of insulin to the monomeric and/or dimeric form of insulin and prevents or minimizes re-association to the hexameric form post injection, thereby promoting rapid absorption into the bloodstream post injection. Variation in EDTA concentration alters the pharmacokinetics and pharmacodynamics of rapid acting insulin formulations. The monomers and dimers are unstable, and require the addition of organic diacids such as citric acid or a salt thereof such as sodium citrate, to bind to the charges exposed during dissociation, thereby stabilizing the monomers and dimers.

A possible explanation for the injection site discomfort of the EDTA-citric acid-insulin formulation is chelation of extracellular calcium by disodium EDTA. Calcium is in the extracellular fluid at a concentration of approximately 1 mM, and is essential for excitation-contraction coupling, muscle function, neurotransmitter release, and cellular metabolism. Loss of local calcium can cause muscle tetany, which is a disorder marked by intermittent tonic muscular contractions, accompanied by fibrillary tremors, paresthesias and muscular pain. To avoid this interaction, a formulation removing calcium from the extracellular fluid should not be used.

The substitution of disodium EDTA with the calcium chelated form of EDTA (i.e., calcium disodium EDTA) can reduce injection site pain as compared to the same amount of disodium EDTA. However, calcium disodium EDTA slightly delays the rate of absorption in vivo. Therefore, magnesium was used instead of calcium to chelate the excess EDTA. The addition of magnesium to the formulation increased injection site tolerability and did not alter the rate of insulin absorption.

I. Definitions

As used herein, "insulin" refers to human or non-human, recombinant, purified or synthetic insulin or insulin analogues, unless otherwise specified.

As used herein, "Human insulin" is the human peptide hormone secreted by the pancreas, whether isolated from a natural source or made by genetically altered microorganisms.

As used herein, an insulin analogue is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine, and insulin detemir. The insulin can also be modified chemically, for example, by acetylation. As used herein, human insulin analogues are altered human insulin which is able to perform the same action as human insulin.

As used herein, a "chelator" or "chelating agent", refers to a chemical compound that has the ability to form one or more bonds to zinc ions. The bonds are typically ionic or coordination bonds. The chelator can be an inorganic or an organic compound. A chelate complex is a complex in which the metal ion is bound to two or more atoms of the chelating agent.

As used herein, a "solubilizing agent", is a compound that increases the solubility of materials in a solvent, for example, insulin in an aqueous solution. Examples of solubilizing agents include surfactants such as polysorbates (TWEEN®); solvents such as ethanol; micelle forming compounds, such as oxyethylene monostearate; and pH-modifying agents.

As used herein, a "dissolution/stabilization agent" or "dissolution/stabilizing agent" is an acid or a salt thereof that, when added to insulin and EDTA, enhances the transport and absorption of insulin relative to HCl and EDTA at the same pH, as measured using the epithelial cell transwell plate assay described in the examples below. HCl is not a dissolution/stabilization agent but may aid in solubilization. Citric acid is a dissolution/stabilization agent when measured in this assay.

As used herein, "inorganic magnesium compound" or "inorganic magnesium salt" refers to compounds in which the anion does not contain one or more carbon atoms.

As used herein, "organic magnesium compound" or "organic magnesium salt" refers to compounds in which the anion contains one or more carbon atoms.

As used herein, an "excipient" is an inactive substance other than a chelator or dissolution/stabilization agent, used as a carrier for the insulin or used to aid the process by which a product is manufactured. In such cases, the active substance is dissolved or mixed with an excipient.

As used herein, a "physiological pH" is between 6.8 and 7.6, preferably between 7 and 7.5, most preferably about 7.4.

As used herein, "Cmax" is the maximum or peak concentration of a drug observed after its administration.

As used herein, "Tmax" is the time at which maximum concentration (Cmax) occurs. As used herein, ½ Tmax is the time at which half maximal concentration (½ Cmax) of insulin occurs in the blood. This may also be expressed as T50% earlymax.

II. Formulations

Formulations include insulin or an insulin analog, a zinc chelator and a dissolution/stabilizing agent(s), one or more magnesium compounds, and, optionally, one or more other excipients. In the preferred embodiment, the formulations are suitable for subcutaneous administration and are rapidly absorbed into the subcutaneous tissue. The choice of dissolution/stabilization agent and chelator, the concentration of both the dissolution/stabilization agent and the chelator, and the pH that the formulation is adjusted to, all have a profound effect on the efficacy of the system. While many combinations have efficacy, the preferred embodiment is chosen for reasons including safety, comfort, stability, regulatory profile, and performance.

In the preferred embodiment, at least one of the formulation ingredients is selected to mask charges on the insulin. This is believed to facilitate the transmembrane transport of the insulin and thereby increase both the onset of action and bioavailability for the insulin. The ingredients are also selected to form compositions that dissolve rapidly in aqueous medium. Preferably the insulin is absorbed and transported to the plasma quickly, resulting in a rapid onset of action, preferably beginning within about 5 minutes following administration and peaking at about 15-30 minutes following administration.

The chelator, such as sodium and/or calcium EDTA, chelates the zinc within the insulin, thereby removing the zinc from the insulin molecule. This causes the hexameric insulin to dissociate into its dimeric and monomeric forms and retards reassembly into the hexamer state post injection. Since these two forms exist in a concentration-driven equilibrium, as the monomers are absorbed, more monomers are created. Thus, as insulin monomers are absorbed through the subcutaneous tissue, additional dimers dissemble to form more monomers. The monomeric form has a molecular weight that is less than one-sixth the molecular weight of the hexameric form, thereby markedly increasing both the speed and quantity of insulin absorption. To the extent that the chelator (such as EDTA) and/or dissolution/stabilization agent (such as citric acid) hydrogen bond with the insulin, it is believed that they mask the charge on the insulin, facilitating its transmembrane transport and thereby increasing both the onset of action and bioavailability of the insulin.

A magnesium salt has been found to not significantly alter the pharmacokinetic profile while at the same time decreasing the injection site pain.

In the preferred embodiment, M-cresol is added for its anti-microbial properties and enhancement of shelf life.

Insulin

Insulin or insulin analogs may be used in this formulation. Preferably, the insulin is recombinant human insulin. Recombinant human insulin is available from a number of sources. The dosages of the insulin depend on its bioavailability and the patient to be treated. Insulin is generally included in a dosage range of between 1.5 and 200 IU, depending on the level of insulin resistance of the individual. Typically, insulin is provided in 100 IU vials, though other presentations of 200, 400 or 500 U/ml are described herein. In the most preferred embodiment the injectable formulation is a volume of 1 ml containing 100 U of insulin. Additional embodiments include higher concentration insulin formulations, the most preferred being U-400.

There are several differing types of commercial insulin available for diabetes patients. These types of insulins vary according to (1) how long they take to reach the bloodstream and start reducing blood glucose levels; (2) how long the insulin operates at maximum strength; and (3) how long the insulin continues to have an effect on blood sugar.

Fast Acting Insulin

Fast acting insulins are intended to respond to the glucose derived from ingestion of carbohydrates during a meal. Fast acting insulins start to work within one to 20 minutes, peaking about one hour later and lasting from three to five hours. Fast acting insulin takes about two hours to fully absorb into the systemic circulation. Fast acting insulins include regular recombinant human insulin (such as HUMULIN®, marketed by Eli Lilly, and NOVALIN®, marketed by Novo Nordisk A/S) which are administered in an isotonic solution at pH 7. Bovine and porcine insulins, which differ in several amino acids to human insulin, but are bioactive in humans, are also fast acting insulins.

Concentrated Insulin Formulations

More concentrated forms of insulin are provided for insulin resistant individuals. The commercially available formulation Humulin R U-500 has a very long duration of action and is suitable for basal use only due to its slow release profiles.

Rapid Acting Insulin.

Some diabetes patients use rapid-acting insulin at mealtimes, and long-acting insulin for 'background' continuous insulin. This group includes insulins that have been modified or have altered locations of amino acids in order to enhance their rate of absorption.

At present there are three types of rapid-acting commercial insulin analogs available: insulin lispro (Lysine-Proline insulin, sold by Eli Lilly as HUMALOG®), insulin glulisine (sold by Sanofi-Aventis as APIDRA®) and insulin aspart (sold by Novo Nordisk as NOVOLOG®).

Intermediate Acting Insulin

Intermediate-acting insulin has a longer lifespan than short-acting insulin but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE insulin. NPH insulin contains protamine which slows down the speed of absorption so that the insulin takes longer to reach the bloodstream but has a longer peak and lifespan. Intermediate acting insulins may be combined with rapid acting insulins at neutral pH, to reduce the total number of injections per day.

Blends of immediate acting insulin and intermediate acting insulin: Blends of rapid acting insulin and NPH insulin are commercially available to fulfill the need for prandial and basal use in a single injection. These insulin blends may be regular recombinant insulin based (HUMULIN® 70/30 (70% human insulin isophane and 30% human insulin, Eli Lilly) or analog based, such HUMALOG®Mix75/25 (75% insulin lispro protamine suspension and 25% insulin lispro solution) (Eli Lilly) and are 100 U-ml. These blends use a protamine insulin suspension (HUMULIN® or HUMALOG® based) to extend the duration of action insulin action with HUMULIN®R (regular human insulin) or HUMALOG®R to cover the prandial needs.

Long Acting Insulin

Examples of long acting insulins are insulin glargine (marketed under the tradename LANTUS®, Sanofi Aventis) and insulin detemir (LEVEMIR®, Novo Nordisk A/S). The extended duration of action of LANTUS® is normally induced by the pH elevation from 4 to 7 post subcutaneous injection. This changes the solubility of the insulin glargine, creating a microprecipitate. This microprecipitate slowly dissolves in the subcutaneous tissue, sustaining its glucose lowering effect for up to 24 hours. It differs from human insulin by having a glycine instead of asparagine at position 21 and two arginines added to the carboxy-terminus of the beta-chain.

Dissolution/Stabilization Agents

Certain polyacids appear to mask charges on the insulin, enhancing uptake and transport, as shown in FIG. 1. Organic polyacids which are effective as dissolution/stabilization agents include acetic acid, ascorbic acid, citric acid, glutamic acid, aspartic acid, succinic acid, fumaric acid, maleic acid, adipic acid, and salts thereof, relative to hydrochloric acid, which is not a charge masking agent. The effective acids are all diacids or polyacids. For example, if the active agent is insulin, a preferred dissolution/stabilization agent is citric acid and/or sodium citrate. Hydrochloric acid may be used for pH adjustment, in combination with any of the formulations, but is not a dissolution/stabilization agent.

The acid may be added directly or in the form of a salt, which dissociates in aqueous solution. Salts of the acids include sodium acetate, ascorbate, citrate, glutamate, aspartate, succinate, fumarate, maleate, and adipate. Salts of organic acids can be prepared using a variety of bases including, but not limited to, metal hydroxides, metal oxides, metal carbonates and bicarbonates, metal amines, as well as ammonium bases, such as ammonium chloride, ammonium carbonate, etc. Suitable metals include monovalent and polyvalent metal ions. Exemplary metals ions include the Group I metals, such as lithium, sodium, and potassium; Group II metals, such as barium, magnesium, calcium, and strontium; and metalloids such as aluminum. Polyvalent metal ions may be desirable for organic acids containing more than carboxylic acid group since these ions can simultaneously complex to more than one carboxylic acid group.

The range of dissolution/stabilization agent corresponds to an effective amount of citric acid in combination with insulin and disodium EDTA. For example, a range of $9.37 \times 10^{-4}$ M to $9.37 \times 10^{-2}$ M citric acid corresponds with a weight/volume of about 0.18 mg/ml to about 18 mg/ml if the citric acid is anhydrous citric acid with a molar mass of approximately 192 gram/mole. In some embodiments the amount of anhydrous citric acid ranges from about 50% of 1.8 mg/ml (0.9 mg/ml) to about 500% of 1.8 mg/ml (9 mg/ml), more preferably from about 75% of 1.8 mg/ml (1.35 mg/ml) to about 300% of 1.8 mg/ml (5.4 mg/ml). In a preferred embodiment, the amount of anhydrous citric acid can be about 1.8 mg/ml, or about 2.7 mg/ml, or about 3.6 mg/ml, or about 5.4 mg/ml. In the most preferred embodiment, the amount of citric acid is 2.7 mg/ml of the injectable formulation. The weight/volume may be adjusted, if for example, citric acid monohydrate or trisodium citrate or another citric acid is used instead of anhydrous citric acid.

The preferred dissolution/stabilization agent when the insulin formulation has a pH in the physiological pH range is sodium citrate.

In a particularly preferred embodiment, the formulation contains a mixture of disodium EDTA and citric acid. In general the ratio of citric acid to disodium EDTA is in the range of 300:100, for example, 100:120, 100:100, 200:100, 150:100, 300:200, and 500:100.

Chelators

In the preferred embodiment, a zinc chelator is mixed with the insulin. The chelator may be ionic or non-ionic. Chelators include ethylenediaminetetraacetic acid (EDTA), typically the sodium and/or calcium salt, EGTA, alginic acid, alpha lipoic acid, dimercaptosuccinic acid (DMSA), CDTA (1,2-diaminocyclohexanetetraacetic acid), and trisodium citrate (TSC). Hydrochloric acid is used in conjunction with TSC to adjust the pH, and in the process gives rise to the formation of citric acid, which is a dissolution/stabilization agent. HCl is not a dissolution/stabilization agent.

The chelator captures the zinc from the insulin, thereby favoring the monomeric or dimeric form of the insulin over the hexameric form and facilitating absorption of the insulin into the tissues surrounding the site of administration (e.g. mucosa, or fatty tissue). In addition, the chelator hydrogen may bond to the insulin, thereby aiding the charge masking of the insulin monomers and facilitating transmembrane transport of the insulin monomers.

In the preferred embodiment, the chelator is EDTA. In the most preferred embodiment, the formulation contains insulin, disodium EDTA, calcium chloride, and a dissolution/stabilization agent such as citric acid or sodium citrate.

A range of $2.42 \times 10^{-4}$ M to $9.68 \times 10^{-2}$ M EDTA corresponds to a weight/volume of about 0.07 mg/ml to about 28 mg/ml if the EDTA is Ethylenediaminetetraacetic acid with a molar mass of approximately 292 grams/mole. Reduction of the concentration of EDTA can slow the rate of insulin absorption and delay the glucose response to the insulin injection. Further increases in this concentration provide negligible gains in absorption rate.

In preferred embodiments, the amount of EDTA ranges from about 5% of 1.8 mg/ml (0.09 mg/ml) to about 500% of 1.8 mg/ml (9 mg/ml), more preferably about 15% of 1.8 mg/ml (0.27 mg/ml) to about 200% of 1.8 mg/ml (3.6 mg/ml). For example, the amount of EDTA can be 0.1 mg/ml, 0.25 mg/ml, 1.0 mg/ml, 1.8 mg/ml, 2.0 mg/ml, or 2.4 mg/ml of EDTA.

Reduction of the concentration of EDTA can slow the rate of insulin absorption and delay the glucose response to the insulin injection. In a preferred embodiment, the chelator is disodium EDTA, preferably, in an amount equal to or less than 2.0 mg/ml. Further increases in this concentration provide negligible gains in absorption rate. In some embodiments, the EDTA is a combination of disodium EDTA and calcium disodium EDTA. For example, in one embodiment, the EDTA is about 0.27-0.3 mg/ml of disodium EDTA in combination with about 1.8-2.0 mg/ml of calcium disodium EDTA. In some embodiments, the EDTA is between about 1.8-2.0 mg/ml of calcium disodium EDTA or disodium EDTA and $CaCl_2$.

Magnesium Compounds

The formulations contain one or more pharmaceutically acceptable magnesium compounds. As discussed above, EDTA can cause irritation at the injection site, possibly due to the complexation of endogenous calcium at the site of administration. While the inclusion of calcium EDTA can ameliorate this irritation, the addition of calcium EDTA to the formulation slows down the insulin absorption. In order to minimize or prevent injection site irritation and not change the rate of subcutaneous absorption, one or more magnesium compounds are incorporated into the formulation.

The magnesium compounds can be an inorganic and/or organic magnesium salt. Suitable magnesium inorganic salts include, but are not limited to, magnesium hydroxide ($Mg(OH)_2$), magnesium sulfate $Mg(SO_4)$, magnesium halides, such as magnesium chloride ($MgCl_2$), magnesium bromide ($MgBr_2$), and magnesium iodide ($MgI_2$); magnesium pyrophosphate, magnesium sulfate heptahydrate, and magnesium oxide ($MgO_2$).

Suitable magnesium organic salts include, but are not limited to, magnesium EDTA, magnesium lactate, amino acid chelates, such as magnesium aspartate; magnesium acetate, magnesium carbonate ($Mg(CO_3)_2$), magnesium citrate, and magnesium gluconate.

In particular embodiments, the one or more magnesium compounds is magnesium EDTA, $Mg(OH)_2$, $MgSO_4$, or combinations thereof. In one embodiment, the one or more magnesium compounds is $MgSO_4$.

The concentration of the one or more magnesium compounds is from about 0.1 to about 10 mg/ml, preferably from about 0.1 to about 5 mg/ml, more preferably from about 0.1 to about 2 mg/ml, most preferably from about 0.2 to about 2 mg/ml. In some embodiments, the formulations contains about 0.2-0.3 mg/ml $Mg(OH)_2$ (e.g., 0.282), about 1.7-2.0 magnesium EDTA (e.g., 1.89), and/or about 0.4-0.5 magnesium sulfate (e.g., 0.481).

Excipients

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In the preferred embodiment, one or more solubilizing agents are included with the insulin to promote rapid dissolution in aqueous media. Suitable solubilizing agents include wetting agents such as polysorbates, glycerin and poloxamers, non-ionic and ionic surfactants, food acids and bases (e.g. sodium bicarbonate), and alcohols, and buffer salts for pH control. In a preferred embodiment the pH is adjusted using hydrochloric acid (HCl) or sodium hydroxide (NaOH). The pH of the injectable formulation is typically between about 6.8-7.8, preferably about 7.1

Stabilizers are used to inhibit or retard drug decomposition reactions which include, by way of example, oxidative reactions. A number of stabilizers may be used. Suitable stabilizers include buffers; such as citrates, phosphates and acetates; polysaccharides, such as cellulose and cellulose derivatives, sulfated polysaccharides complex and simple alcohols, such as glycerol (or glycerin, or glycerine); bacteriostatic agents such as phenol, benzyl alcohol, meta-cresol (m-cresol), 2-phenoxyethanol and methyl/propyl paraben; isotonic agents, such as sodium chloride, glycerol (or glycerin, or glycerine), cyclic amino acids, amino acids and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins. Also, solvent or co-solvent systems (ethanol, PEGable preparations prior to adding the chelator and dissociating/stabilizing agents described herein.

Examples of formulations are described in detail in the Examples below. Calcium-EDTA-citric acid formulations contain: 100 U/ml of insulin, 1.8 mg/ml of calcium disodium EDTA, 2.7 mg/ml of citric acid, 20.08 mg/ml of glycerin, and 3.0 mg/ml of m-cresol ("BIOD-105 or 100 U/ml of insulin or an insulin analog, 1.8 mg/ml of disodium EDTA, 2.7 mg/ml of citric acid, 18.1 mg/ml of glycerin, 2.0 mg/ml of m-cresol, and 5 mM of calcium chloride ("BIOD-107").

Insulin formulations containing one or more magnesium compounds were prepared as described in Table 1.

TABLE 1

Magnesium-EDTA-Insulin Formulation Compositions

| Form | Insulin | IU/ml | Na2EDTA mg/ml | Mg(OH2)2 mg/ml | MgEDTA mg/ml | Citric Acid mg/ml | NaCitrate | Glycerin mg/ml | M-Cresol mg/ml | phenol | Disodium phosphate | ZnO | A3 mg/ml | MgSO4 mg/ml |
|---|---|---|---|---|---|---|---|---|---|---|---|---|---|---|
| Linjeta | RHI | 100 | 1.8 | | | 1.8 | | 22 | 3 | — | — | | | |
| BIOD-120 | RHI | 100 | 1.8 | | | 1.8 | | 22 | 3 | | | | | 0.481 (4 mM) |
| BIOD 121 | RHI | 100 | 1.8 | | | 1.8 | | 18 | 3 | | | | 0.3 | 0.481 (4 mM) |
| BIOD-123 | RHI | 100 | 1.5 | | | 1.5 | | 22 | 3 | | | | | 0.481 (4 mM) |
| BIOD-126 | RHI | 100 | | | 1.89 | 1.8 | | 22 | 3 | | | | | |
| BIOD-127/128 | RHI | 100 | 1.8 | 0.282 | | 1.8 | | 22 | 3 | | | | | |
| BIOD-250 | IL | 100 | 0.45 | | | | 2.4 | 16 | 3.15 | .01 | 1.88 | .0197 | | .481 |
| BIOD-531 | RHI | 400 | 3.6 | | | 1.8 | | 16 | 2 | | | | | .481 |

IL = Insulin Lispro; RHI = Recombinant human insulin 300, glycerin, propylene glycol) and solubilizing agents such as polysorbates 20/80; poloxamer 188 and sorbitol. In one example, the stabilizer may be a combination of glycerol, bacteriostatic agents and isotonic agents. The most preferred formulations include glycerin and m-cresol. The range for glycerin is about 1-35 mg/ml, preferably about 10-25 mg/ml, most preferably about 19.5-22.5 mg/ml. The range for m-cresol is about 0.75-6 mg/ml, preferably about 1.8-3.2 mg/ml, most preferably about 2 or 3 mg/ml. Calcium chloride can be added to the formulation to "neutralize" any free EDTA and sodium citrate and/or citric acid is added to stabilize the dissociated monomer. Calcium chloride is more typically added to the formulation when the chelator is disodium EDTA. It is added in matched approximately equimolar concentration to the disodium EDTA. For example, if the disodium EDTA is 5 mM, then 5 mM calcium chloride should be used. The effective range is 80-120% of disodium EDTA. A further possible candidate for this is magnesium, added in similar quantities. The range for calcium chloride is about 0.1-10 mM, preferably more preferably about 2.5-7.5 mM, most preferably about 5 mM.

In some embodiments, commercial preparations of insulin and insulin analogs preparations can be used as the insulin of the formulations disclosed herein. Therefore, the final formulation can include additional excipients commonly found in the commercial preparations of insulin and insulin analogs, including, but not limited to, zinc, zinc chloride, phenol, sodium phosphate, zinc oxide, disodium hydrogen phosphate, sodium chloride, tromethamine, and polysorbate 20. These may also be removed from these commercially avail- III. Methods of Making the Formulations In a preferred embodiment, the injectable formulation contains insulin, disodium and/or calcium disodium EDTA, citric acid, saline or glycerin, m-Cresol and chloride magnesium salt. In the most preferred embodiment, the subcutaneous injectable formulation is produced by combining water, disodium EDTA, magnesium salt such as MgSO$_4$, citric acid, glycerin, m-Cresol and insulin by sterile filtration into multi-use injection vials or cartridges.

Methods of making the injectable insulin formulations are described in detail in the Examples below.

In one embodiment, the EDTA is added to the formulation(s) prior to the citric acid. In another embodiment, sodium citrate is added instead of citric acid. In the preferred embodiment, citric acid is added to the formulation(s) prior to the EDTA. In one preferred embodiment, the components of the formulation are added to water: citric acid, EDTA, glycerin, m-Cresol, magnesium salt and insulin. Glycerol and m-Cresol are added as a solution while citric acid, EDTA and magnesium salt may be added as powder, crystalline or pre-dissolved in water In some embodiments, the subcutaneous injectable formulation is produced by mixing water, citric acid, EDTA, glycerin and m-Cresol to form a solution (referred to as the "diluent") which is filtered and sterilized. The insulin is separately added to water, sterile filtered and a designated amount is added to a number of separate sterile injection bottles which is then lyophilized to form a powder. The lyophilized powder is stored separately from the diluent to retain its stability. Prior to administration, the diluent is added to the insulin injection bottle to dissolve the insulin and create the final reconstituted product.

In another embodiment, the insulin is in solution and the excipients are lyophilized, spray dried and added to the insulin prior to injection. In yet another embodiment, the excipients are made as a concentrated liquid and introduced to the liquid insulin prior to injection.

After the predetermined amount of insulin is subcutaneously injected into the patient, the remaining insulin solution may be stored, preferably with refrigeration. In a preferred embodiment, the insulin is prepared as an aqueous solution at about pH 7.0, in vials or cartridges and kept at 4° C.

IV. Methods of Using Formulations

The formulations may be injected subcutaneously or intramuscularly. The formulation is designed to be rapidly absorbed and transported to the plasma for systemic delivery.

Formulations containing insulin as the active agent may be administered to type 1 or type 2 diabetic patients before or during a meal. Due to the rapid absorption, the compositions can shut off the conversion of glycogen to glucose in the liver, thereby preventing hyperglycemia, the main cause of complications from diabetes and the first symptom of type 2 diabetes. Currently available, standard, subcutaneous injections of human insulin must be administered about one half to one hour prior to eating to provide a less than desired effect, because the insulin is absorbed too slowly to shut off the production of glucose in the liver. These new ultrarapid acting formulations may be taken closer to the meal. A potential benefit to this formulation with enhanced pharmacokinetics may be a decrease in the incidence or severity of obesity that is a frequent complication of insulin treatment.

EXAMPLE 1

Effect of Calcium Disodium EDTA Concentration on Injection Site Discomfort in Humans Materials and Methods Each milliliter of VIAJECT® 7 (VJ 7) contains: 3.7 mg (100 IU) of recombinant human insulin, 1.8 mg of citric acid, 1.8 mg of disodium EDTA, 22.07 mg of glycerin, 3.0 mg of m-Cresol as a preservative, and sodium hydroxide and/or hydrochloric acid to adjust the pH to approximately 7.

Each milliliter of BIOD 102 contains: 3.7 mg (100 IU) of recombinant human insulin, 1.8 mg of citric acid, 2.4 mg of calcium disodium EDTA, 15.0 mg of glycerin, 3.0 mg of m-cresol as a preservative, and sodium hydroxide and/or hydrochloric acid to adjust the pH to approximately 7.1.

Each milliliter of BIOD 103 contains: 3.7 mg (100 IU) of recombinant human insulin, 1.8 mg of citric acid, 0.25 mg of disodium EDTA, 2.0 mg of calcium disodium EDTA, 15.0 mg of glycerin, 3.0 mg of m-cresol as a preservative, and sodium hydroxide and/or hydrochloric acid to adjust the pH to approximately 7.1.

Each solution was injected subcutaneously into a human volunteer and the volunteer was asked to rate the pain associated with the injection.

Basic pharmacokinetic parameters Cmax, Tmax, and ½ Tmax were estimated without non-linear modeling A t-test was performed on the data from each formulation compared to VJ7.

Results

As shown in Table 2, the samples containing calcium disodium EDTA (BIOD 102 and BIOD 103) had slightly lower Cmax and later Tmax than the samples containing only disodium EDTA (VJ 7).

TABLE 2

Comparison of calcium disodium EDTA with disodium EDTA Pharmacokinetic Data

| Variable | BIOD 102 | BIOD 103 | VIAJECT® 7 (VJ7) | BIOD 102 vs VJ7 Ratio/Difference (CI) | BIOD 103 vs VJ7 Ratio/Difference (CI) |
|---|---|---|---|---|---|
| $AUC_{0-480}$ | 10005.6 | 10139.6 | 9844.8 | 1.02 (0.98, 1.06) | 1.03 (0.99, 1.07) |
| Cmax | 54.0 | 53.4 | 66.1 | 0.82 (0.68, 0.98) | 0.81 (0.68, 0.96) |
| $T_{50\%}$ (Early) | 12.9 | 17.3 | 11.0 | 1.9 (-3.0, 6.8) | 6.4 (1.8, 11.0) |
| Tmax | 73.1 | 63.9 | 34.2 | 38.9 (17.0, 60.8) | 29.7 (9.0, 50.1) |
| $T_{50\%}$ (Late) | 210.6 | 206.4 | 116.4 | 94.2 (49.6, 138.8) | 90.0 (48.2, 131.7) |

VIAJECT® 7: 1.8 mg of disodium EDTA
BIOD 102: 2.4 mg of calcium disodium EDTA
BIOD 103: 0.25 mg of disodium EDTA, 2.0 mg of calcium disodium EDTA These results demonstrate that the calcium formulations have a significantly slower rate of uptake than the original insulin, sodium EDTA, citric acid formulation, as indicated by the mean times to half maximal insulin concentrations and the time to maximal insulin concentrations (Table 2).

Injection of the insulin formulations containing calcium disodium EDTA resulted in significantly less injection site pain than the disodium EDTA samples, as shown by Table 3.

TABLE 3

Injection Site Discomfort Data

| Variable | BIOD 102 | BIOD 103 | VIAJECT® 7(VJ7) | BIOD 102 vs VJ7 p-value | BIOD 103 vs VJ7 p-value |
|---|---|---|---|---|---|
| VAS | 7.7 | 12.4 | 21.0 | 0.026 | 0.109 |
| Severity | 0.55 | 0.56 | 1.10 | 0.030 | 0.025 |
| Relative | 2.84 | 2.98 | 3.58 | 0.023 | 0.244 |

VAS: 0 = None; 100 = Worst possible; VR Absolute Discomfort: 0 = None, 1 = Mild, 2 = Moderate, 3 = Severe
VR Relative (to usual injections): 1 = Much less; 2 = Less; 3 = Equal; 4 = Increased; 5 = Much increased

EXAMPLE 2

Study of the Rate of Insulin Absorption of Formulations BIOD 105 and BIOD 107 in Miniature Diabetic Swine The aim of this study was to evaluate the pharmacokinetic (PK) and pharmacodynamic (PD) properties of modified insulin formulations predicted to be associated with improved toleration. The addition of calcium EDTA to an insulin formulation (containing disodium EDTA) was shown in Example 1 to reduce the site reaction to the injection when compared to an insulin formulation containing disodium EDTA, without added calcium EDTA); however, the rapid action of the formulation was somewhat delayed from this substitution. Therefore, new insulin formulations were developed to regain the rapid uptake and to improve stability. Additional citric acid was added (150% compared to the original formulation, VJ 7) to some formulations, and a ⅓ reduction in m-cresol was explored, to enhance stability.

In one of the new formulations, disodium EDTA and $CaCl_2$ were added as separate excipients to achieve the calcium chelated form of EDTA (BIOD 107). The rate of insulin absorption from BIOD 107 was compared to the rate of insulin absorption from an insulin formulation to which Ca EDTA (BIOD 105) was added directly, and to the rate of insulin absorption from VJ 7 (containing disodium EDTA, no added calcium).

Methods and Materials

Calcium-EDTA-citric acid formulation (BIOD 105) contains: 100 U/ml of insulin, 1.8 mg/ml of calcium disodium EDTA, 2.7 mg/ml of citric acid (=150% the amount in VJ 7), 20.08 mg/ml of glycerin, and 3.0 mg/ml of m-cresol.

$CaCl_2$-EDTA-citric acid formulation (BIOD 107) contains: 100 U/ml of insulin or an insulin analog, 1.8 mg/ml of disodium EDTA, 2.7 mg/ml of citric acid (=150% the amount in VJ 7), 18.1 mg/ml of glycerin, 2.0 mg/ml of m-cresol (=⅓ reduction in amount of m-cresol in VJ 7), and 5 mM of calcium chloride.

The formulations, VJ 7, BIOD 105 and 107, were subcutaneously injected into miniature swine, following which the rate of insulin absorption following subcutaneous administration of each test formulation was measured.

Six to eight diabetic miniature swine were injected in the morning with 0.25 U/kg of test formulation instead of their daily porcine insulin. Animals were fed 500 g of swine diet and plasma samples were collected at −30, −20, −10, 0, 5, 10, 15, 20, 30, 45, 60, 75, 90, 120, 150, 180, 240, 300 and 360 min post dose using a Becton Dickinson $K_2$EDTA vacutainer. Frozen plasmas were assayed for insulin content (#EZHI-14K Millipore, USA) and analyzed for glucose concentration (YSI 3200 analyzer, YSI Life sciences, USA).

Duration was estimated without non-linear modeling. The pharmacodynamic response was calculated from the time post dose required to drop the blood glucose level 20 points from baseline and the time for blood glucose to increase 20 points from nadir. The time between these parameters is defined as duration of action.

Absorption rate was calculated as the slope of line drawn from the initial increase in insulin concentration post injection (up to 30 min. post dose).

Results:

Absorption rate parameters are shown below in Table 4:

TABLE 4

Comparison of the initial rate of absorption of formulations BIOD 105 and BIOD 107 to the original formulation VJ7.

|  | Abs. Rate (µU/mL/min) | Time to 20 pt drop (min.) |
|---|---|---|
| VJ 7 | 5.9 ± 1.6 | 7.4 ± 2.8 |
| BIOD-105 | 4.9 ± 2.2 | 8.5 ± 2.0 |
| BIOD-107 | 4.6 ± 1.5 | 5.5 ± 2.6 |

Time to 20 pt drop = time post dose to drop blood glucose concentration 20 points below baseline T-test comparisons showed that there is no statistical difference in the initial rate of absorption of these formulations. Although the shape of the curves in a plot of the concentration versus time profiles were slightly different, the initial rate of absorption curves were mostly superimposable.

Pharmacodynamic results are shown in Table 5 below.

TABLE 5

Pharmacodynamic parameter calculation.

|  | VJ7 | BIOD 105 | BIOD 107 |
|---|---|---|---|
| Time to 20 pt drop (min.) | 7.0 ± 1.1 | 8.6 ± 0.8 | 5.5 ± .9 |
| Time to 20 pt recovery (min.) | 193.3 ± 47.0 | 222.4 ± 67.3 | 186.3 ± 39.3 |
| Duration (min) | 186.8 ± 47.2 | 213.7 ± 67.6 | 180.8 ± 38.7 |

Time to 20 pt drop = time post dose to drop blood glucose concentration 20 points below baseline
Time to 20 pt recovery = time post dose for blood glucose to increase 20 point post nadir Duration is the time between time to 20 pt drop and time to 20 pt recovery.

The data shows pharmacokinetically and pharmacodynamically absorption profiles similar to the original formulation were achieved, despite substitution of disodium EDTA with calcium disodium EDTA and increased citrate ions.

EXAMPLE 3

Insulin Formulations Containing Magnesium Salts

The effect of magnesium salts on the pharmacokinetics, pharmacodynamics and injection site discomfort obtained with insulin formulations containing disodium EDTA was assessed, compared to HUMLAOG®. Each milliliter of HUMLAOG® contains: insulin lispro 100 units, 16 mg glycerin, 1.88 mg dibasic sodium phosphate, 3.15 mg Metacresol, zinc oxide content adjusted to provide 0.0197 mg zinc ion, trace amounts of phenol, and water for Injection. Insulin lispro has a pH of 7.0 to 7.8. The pH is adjusted by addition of aqueous solutions of hydrochloric acid 10% and/or sodium hydroxide 10%.

Materials and Methods

Insulin formulations were prepared as described above in Table 1.

The formulations were evaluated in 12 human volunteers. The Demographic/Baseline information and Dose Summary are described in Table 6.

TABLE 6

| Demographic/Baseline and Dose Summary | | |
|---|---|---|
| Variable | Statistic/Category | |
| Sex | Female (%) | 2 (16.7%) |
| | Male (%) | 10 (83.3%) |
| Race | Black/African American | 1 (8.3%) |
| | White | 11 (91.7%) |
| Ethnicity | Hispanic/Latino | 2 (16.7%) |
| | Not Hispanic/Latino | 10 (83.3%) |
| Age (yrs) | Mean ± SD | 42.3 ± 8.9 |
| | Median | 43 |
| | Minimum, Maximum | 25, 58 |
| HbA1c (%) | Mean ± SD | 7.70 ± 0.79 |
| | Median | 7.8 |
| | Minimum, Maximum | 6.6, 8.8 |
| Dose (Units) | Mean ± SD | 16.3 ± 2.7 |
| | Median | 17 |
| | Minimum, Maximum | 11, 20 |

Results

The pharmacokinetics (Mean±SE) for BIOD 123, BIOD 125, and HUMLAOG® are shown in Table 7.

With respect to EDTA and Magnesium, BIOD-123 (shown in Table 1) contains disodium EDTA and MgSO$_4$, while BIOD-125 contains disodium EDTA (1.98 mg/ml); citric acid (2.7 mg/ml); glycerin (18 mg/ml); m-cresol (3 mg/ml); CaCl$_2$ (3.38 mg/ml); tween (1.53 mg/ml) and no magnesium compounds.

TABLE 7

| | Pharmacokinetics (Mean ± SE) | | |
|---|---|---|---|
| Variable | BIOD-123 (n = 11) | BIOD-125 (n = 12) | HUMLAOG ® (n = 12) |
| Tins 50% (Early) | 9.8 ± 1.1 | 12.4 ± 2.0 | 27.0 ± 2.7 |
| TinsMax | 46.4 ± 14.9 | 60.8 ± 15.2 | 65.0 ± 7.0 |
| Tins 50% (Late) | 206.2 ± 34.5 | 179.2 ± 40.5 | 151.2 ± 11.0 |
| Cmax | 92.7 ± 17.3 | 75.9 ± 14.3 | 75.0 ± 8.8 |
| AUCins0-30 | 1803 ± 372 | 1331 ± 320 | 532 ± 107 |
| AUCins0-45 | 2926 ± 563 | 2182 ± 472 | 1404 ± 216 |
| AUCins0-60 | 3901 ± 710 | 2993 ± 611 | 2369 ± 314 |
| AUCins0-120 | 7166 ± 950 | 5966 ± 987 | 5663 ± 644 |
| AUCins0-480 | 14705 ± 699 | 13220 ± 1493 | 9080 ± 952 |
| AUCins120-480 | 7539 ± 887 | 7254 ± 1111 | 3417 ± 536 |

With respect to Tables 7 and 9, AUCins0-30=the 0-30 min area under the curve for insulin; AUCins0-45=the 0-45 min area under the curve for insulin; AUCins0-60=the 0-60 min area under the curve for insulin; AUCins0-120=the 0-120 min area under the curve for insulin; AUCins0-480=the 0-480 min area under the curve for insulin; AUCins120-480=the 120-480 min area under the curve for insulin.

The time related pharmacokinetic (PK) parameters (medians) are shown in Table 8.

TABLE 8

| Time-Related PK Parameters (Medians) | | | |
|---|---|---|---|
| Variable | BIOD-123 | BIOD-125 | HUMLAOG ® |
| Tins 50% (Early) | 9.6 | 9.4 | 25.9 |
| TinsMax | 25.0 | 30.0 | 67.5 |
| Tins 50% Late | 169.7 | 140.0 | 149.8 |

The pharmacodynamics (LS means) are show in Table 9.

TABLE 9

| | Pharmacokinetics (LS means) | | | | |
|---|---|---|---|---|---|
| Variable | BIOD-123 | BIOD-125 | HUMLAOG ® | P-Value BIOD-123 vs HUMLAOG ® | P-Value BIOD-125 vs HUMLAOG ® |
| Tins 50% Early | 10.0 | 12.4 | 27.0 | <0.001 | <0.001 |
| TinsMax | 48.0 | 60.8 | 65.0 | 0.256 | 0.769 |
| Tins 50% Late | 210.5 | 179.2 | 151.2 | 0.117 | 0.431 |
| Cmax | 89.5 | 75.9 | 75.0 | (0.264) | (0.942) |
| AUCins0-30 | 1779.8 | 1331.0 | 532.3 | (0.012) | (0.225) |
| AUCins0-45 | 2872.7 | 2181.5 | 1403.5 | (0.002) | (0.056) |
| AUCins0-60 | 3816.6 | 2993.0 | 2369.4 | (0.009) | (0.210) |
| AUCins0-120 | 6942.0 | 5965.7 | 5663.0 | (0.191) | (0.020) |
| AUCins0-480 | 14519 | 13220 | 9080 | (<0.001) | (0.005) |
| AUCins120-480 | 7493.2 | 7254.1 | 3417.0 | (<0.001) | (<0.001) |

P-values in parentheses were not planned and may not be valid because of differences between insulin and lispro assays. AUCins0-45 was unplanned.

TABLE 10

| | Pharmacodynamics (LS means) | | | | |
|---|---|---|---|---|---|
| Variable | BIOD-123 | BIOD-125 | HUMLAOG ® | BIOD-123 vs HUMLAOG ® | P-value BIOD-125 vs HUMLAOG ® |
| GIRmax (mg/kg/min) | 7.00 | 6.49 | 7.28 | 0.752 | 0.358 |
| TGIRmax (min) | 132.6 | 201.1 | 134.3 | 0.961 | 0.049 |

TABLE 10-continued

| | | | Pharmacodynamics (LS means) | | |
|---|---|---|---|---|---|
| Variable | BIOD-123 | BIOD-125 | HUMLAOG ® | P-value BIOD-123 vs HUMLAOG ® | P-value BIOD-125 vs HUMLAOG ® |
| TGIRearly 50% (min) | 32.9 | 34.2 | 43.2 | 0.119 | 0.148 |
| TGIRlate 50% (min) | 289.1 | 283.5 | 260.7 | 0.281 | 0.385 |
| GIRAUC0-30 (mg/kg) | 37.0 | 40.1 | 32.8 | 0.818 | 0.680 |
| GIRAUC0-60 (mg/kg) | 196.0 | 177.4 | 153.5 | 0.305 | 0.547 |
| GIRAUC0-120 (mg/kg) | 493.5 | 423.1 | 504.4 | 0.904 | 0.357 |
| GIRAUC0-180 (mg/kg) | 802.1 | 717.0 | 859.7 | 0.681 | 0.298 |
| GIRAUC0-480 (mg/kg) | 1575.7 | 1469.1 | 1466.0 | 0.571 | 0.987 |
| GIRAUC180-480 (mg/kg) | 781.4 | 752.0 | 606.3 | 0.053 | 0.091 |

Figure 2:
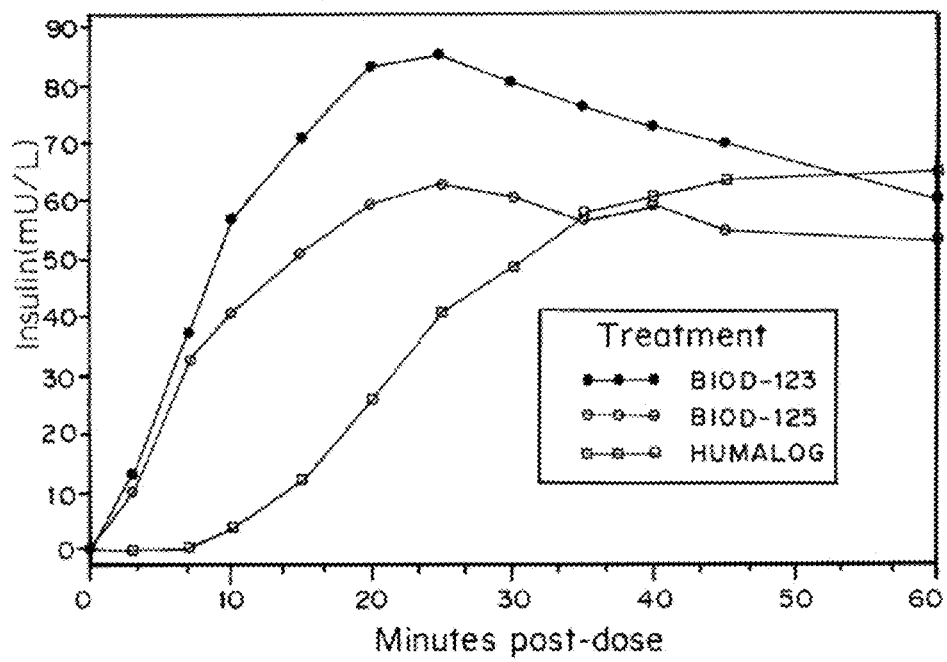
FIGS. 2 and 3 are graphs of mean insulin concentration (mU/L) as a function of time (FIG. 2, 0-60 minutes.
Figure 3:
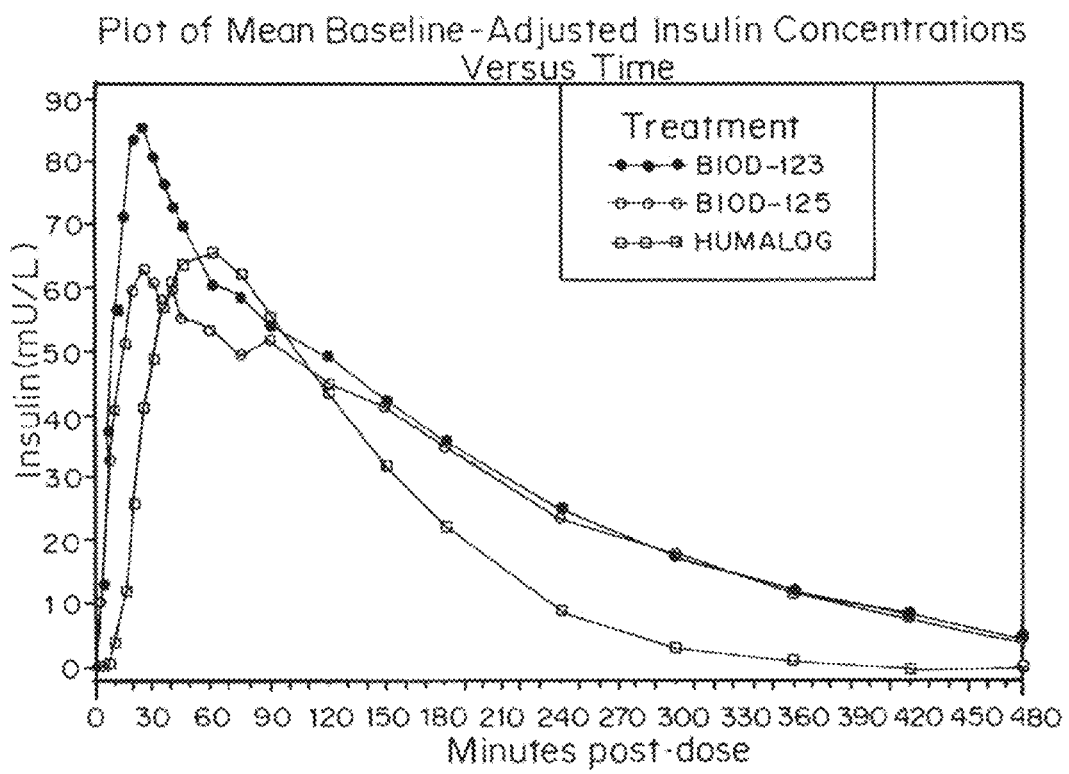

GIR is the glucose infusion rate (mg/kg/min), or amount of glucose required to clamp a subject within a normoglycemic range, typically 80-120 mg/dL following an insulin injection. The GIRmax is the maximal glucose infusion rate, which occurs at TGIRmax. The Half maximal rate occurs before the peak (GIRearly50%) and after the peak (GIRlate50%), at TGIR50% early and TGIR50% late. Areas under the GIR curve are estimated for the entire study duration GIRAUC0-480 (mg/kg) and segments of time between the beginning and end of the study, 0-30, 0-60, 0-120, 0-180, and 180-480 minutes. Graphic representation of the mean concentration versus time profiles from time 0-60 min and 0-480 min are shown in FIGS. 2 and 3, respectively.

Figure 4:
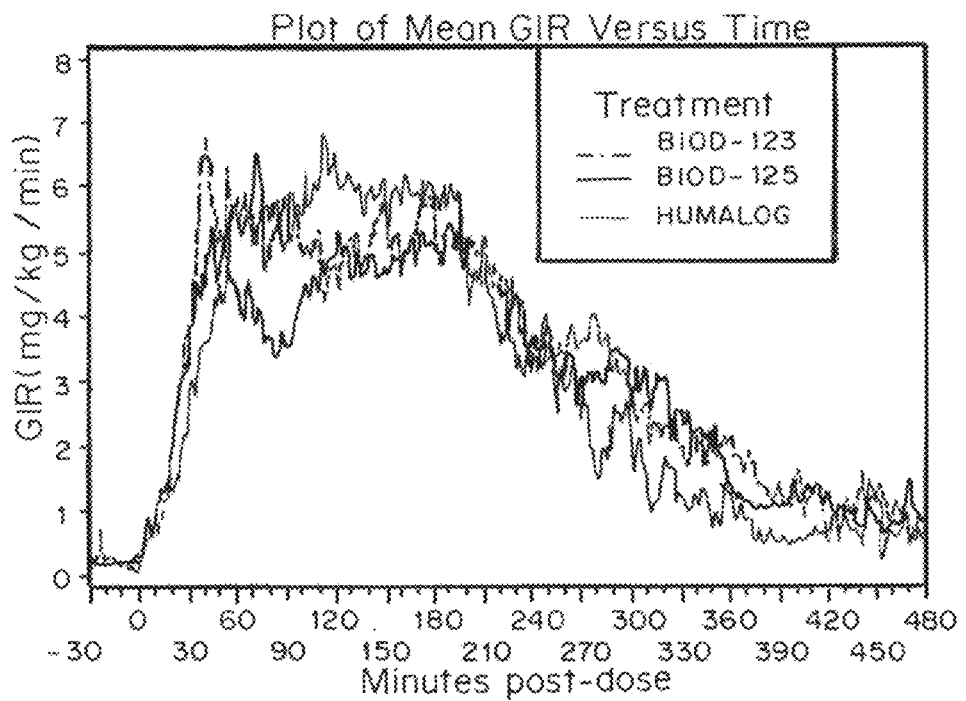
FIGS. 4 and 5 are graphs of mean GIR (mg/kg/min) as a function of time (minutes) of the Mg EDTA insulin formulations BIOD 123 and 125 compared to HUMALOG®.
Figure 5:
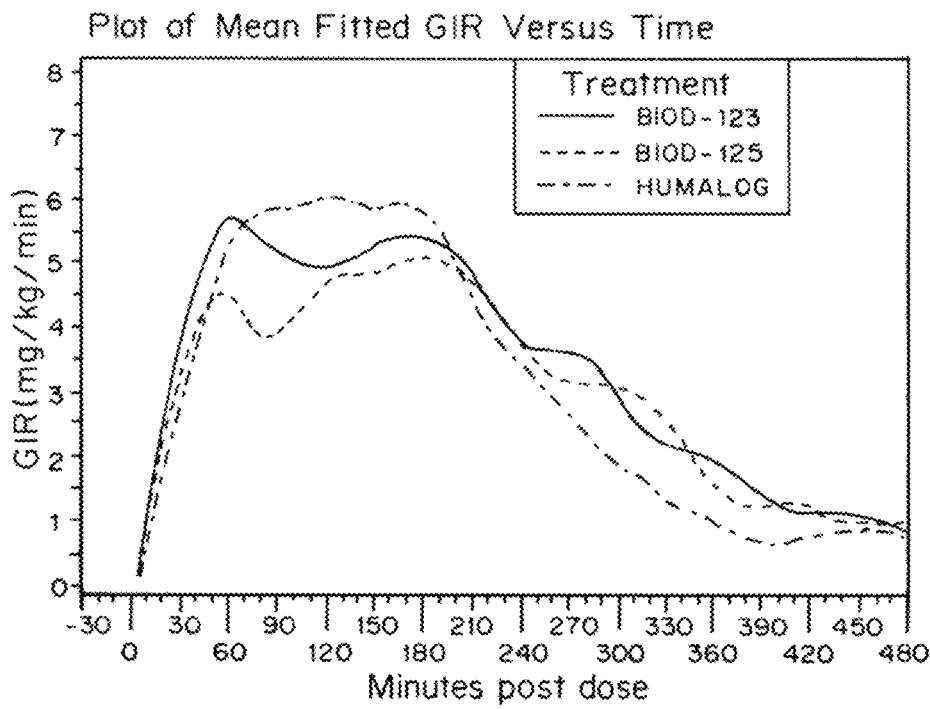

FIGS. 4 and 5 are graphs of mean GIR (mg/kg/min) as a function of time (minutes) of the insulin formulations BIOD 123 and 125 compared to Humalog.

As shown in Tables 7-10 and FIGS. 2-5, BIOD-125 (which contains disodium EDTA, $CaCl_2$ and no magnesium compounds) showed more rapid in vivo absorption than BIOD-123 (which contains disodium EDTA and $MgSO_4$).

Information regarding injection site discomfort is shown in the following tables. Table 11 shows Injection Site Discomfort Results—Safety Population (LS means) and severity of injection site discomfort.

TABLE 11

| | Injection Site Discomfort Results-Safety Population (LS means) and Severity of Injection Site discomfort | | | | |
|---|---|---|---|---|---|
| Variable | BIOD-123 | BIOD-125 | HUMLAOG ® | BIOD-123 vs HUMLAOG ® | BIOD-125 vs HUMLAOG ® |
| VAS | 2.9 | 6.8 | 2.1 | 0.600 | 0.023 |
| Severity Score (absolute) | 0.32 | 0.50 | 0.17 | 0.376 | 0.059 |
| Severity Score (relative) | 2.92 | 3.08 | 2.85 | 0.749 | 0.424 |
| | Injection Site Discomfort Severity | | | | |
| Treatment | | | | | |
| None | 7 (63.4%) | 7 (58.3%) | 10 (83.3%) | | |
| Mild | 4 (36.4%) | 4 (33.3%) | 2 (16.7%) | | |
| Moderate | 0 | 1 (8.3%) | 0 | | |
| Severe | 0 | 0 | 0 | | |

Note:
VAS 0 = No Discomfort, 100 = Worst Possible; Severity 0 = None, 1 = Mild, etc.; Relative Discomfort 2 = Less than Usual, 3 = Equal to Usual, etc.
VAS Results (Arithmetic Mean ± SE); BIOD-123 = 3.6 ± 2.; BIOD-125 = 6.8 ± 2.9;Humalog = 1.8 ± 1.1

Table 12 shows the injection site discomfort relate to usual meal time insulin injection.

TABLE 12

Injection Site Discomfort Relative to Usual Meal Time Insulin Injection

| Treatment | Much Less | Less | Equal | Increased | Greatly Increased |
|---|---|---|---|---|---|
| BIOD-123 (n = 12) | 1 (9.1%) | 1 (9.1%) | 7 (63.4%) | 2 (18.2%) | 0 |
| BIOD-125 (n = 12) | 1 (8.3%) | 0 | 9 (75.0%) | 1 (8.3%) | 1 (8.3%) |
| HUMLAOG ® (n = 12) | 0 | 1 (8.3%) | 11 (91.7%) | 0 | 0 |

Information regarding the type of discomfort, the time of onset, and the duration are shown in Table 13.

TABLE 13

Injection Site Discomfort Description

| Treatment | Irritation (Burning) | Other | Pain (Stinging) |
|---|---|---|---|
| BIOD-123 | 2 | 0 | 2 |
| BIOD-125 | 1 | 2 | 2 |
| HUMLAOG ® | 1 | 0 | 1 |

Injection Site Discomfort Onset

| Treatment | <10 sec | 10 sec-1 min | 1-10 min |
|---|---|---|---|
| BIOD-123 | 3 | 0 | 1 |
| BIOD-125 | 1 | 4 | 0 |
| HUMLAOG ® | 1 | 1 | |

Injection Site Discomfort Duration

| Treatment | ≤30 sec | >30 sec-<5 min |
|---|---|---|
| BIOD-123 | 2 | 2 |
| BIOD-125 | 0 | 5 |
| HUMLAOG ® | 1 | 1 |

As shown above, the formulation containing a magnesium compound (BIOD-123, MgSO$_4$), showed significantly less injection site discomfort than the corresponding compound without MgSO$_4$ (BIOD-125). The duration of discomfort for BIOD-123 was significantly less than for BIOD-125 (Table 13).

EXAMPLE 4

Human Study with BIOD-250 and BIOD-238 Demonstrating Reduced Injection Site Pain and Ultra-rapid Action A Phase 1 clinical trial of two ultra-rapid-acting insulin analog-based formulations, BIOD-238 and BIOD-250, evaluated the pharmacokinetic and injection site toleration profiles relative to HUMALOG® (insulin lispro), a rapid-acting insulin analog. BIOD-238 and BIOD-250 are combinations of Biodel's proprietary excipients with the marketed formulation of HUMALOG®. The composition of BIOD-250 is shown in Table 1. BIOD-238 has similar composition except it does not have magnesium, and has less EDTA (0.225 mg/ml). The excipients used to make BIOD-2338 and BIOD-250 may be added to a bottle of HUMALOG® or made from scratch using insulin lispro API. Either way, the additional components are the same: 100 U/ml insulin lispro, 16 ml/ml glycerin, 3.14 mg/ml m-cresol, 0.0197 mg/ml zinc oxide, 1.88 mg/ml dibasic sodium phosphate, and phenol. HCl and NaOH are used to adjust pH 7.0-7.8 (the pH in the manufactured bottle is 7.5).

The single-center, randomized, double-blind, three-period crossover trial in 12 patients with Type 1 diabetes was conducted in Australia. Each study drug was administered subcutaneously on separate days. Pharmacokinetic measurements were made using an assay to quantify the active ingredients in the study drugs and HUMALOG®. The clinical trial was powered to measure differences in time to half-maximal insulin concentrations. The hypothesis tested in this study was that Biodel's formulations of HUMALOG® would have ultra-rapid absorption profiles with comparable declines from peak concentration and comparable injection site tolerability profiles relative to HUMALOG®. Two approaches were taken to mitigate injection site discomfort—reducing disodium EDTA concentrations (BIOD-238) and addition of magnesium sulfate (BIOD-250), which was observed to improve toleration in a previous study.

The pharmacokinetic profiles of BIOD-238 and BIOD-250 were consistent with the target product profile for analog-based ultra-rapid-acting insulin. Absorption rates of BIOD-238 and BIOD-250 were significantly more rapid than that of HUMALOG®, as indicated by 35-45% reductions in mean times to half maximal insulin concentrations ($p<0.001$ for BIOD-238 and $p=0.001$ for BIOD-250 versus HUMALOG®) and time to maximal insulin concentrations ($p=0.013$ for BIOD-238 and $p=0.025$ for BIOD-250 versus HUMALOG®). Furthermore, the total amount of insulin absorbed over the first 30 minutes following injection of BIOD-238 and BIOD-250 was approximately double that seen for HUMALOG® ($p<0.001$ for BIOD-238 and $p=0.002$ for BIOD-250 versus HUMALOG®). The decline from peak concentration, as indicated by time to half maximal concentration after the peak, was significantly shorter for both BIOD-238 and BIOD-250 compared to HUMALOG® ($p=0.009$ for BIOD-238 and $p=0.016$ for BIOD-250 versus HUMALOG®).

Local injection site discomfort was measured with a 100 mm visual analog scale (VAS) and patient questionnaires. 100 mm is defined as the worst possible discomfort and 0 mm is defined as having no discomfort. In the trial, the VAS score was numerically lower, but not significantly different for BIOD-250 compared to HUMALOG® (mean VAS scores of 2.7 mm and 8.2 mm for BIOD-250 and HUMALOG®, respectively; p=NS). The VAS score for BIOD-238 was significantly higher than that associated with HUMALOG® (mean VAS score of 24.2 mm, p=0.029 versus HUMALOG®). The pharmacokinetic profiles of BIOD-238, BIOD-250 and HUMALOG® as well as their Injection Site Toleration Profiles are shown in Tables 14 and 15, respectively.

TABLE 14

Pharmacokinetic Profiles of BIOD-238, BIOD-250 and HUMALOG®
Table 14: Pharmacokinetic Parameters, Arithmetic Means ± SEM [Median]

| Parameter | BIOD-238 (n = 10) | BIOD-250 (n = 11) | Humalog® (n = 10) | P-value BIOD-238 v Humalog® | P-value BIOD-250 v Humalog® |
|---|---|---|---|---|---|
| $T_{ins\ 50\%\ Early}$ (min) | 13.7 ± 1.9 [13.6] | 14.6 ± 1.9 [12.9] | 24.8 ± 2.9 [22.6] | <0.001 | 0.001 |
| $T_{insMax}$ (min) | 35.5 ± 2.5 [37.5] | 40.9 ± 6.1 [40.0] | 62.5 ± 8.4 [60.0] | 0.013 | 0.025 |
| $AUC_{ins\ 0-30\ min}$ (mU * min/L) | 1278 ± 164 [1105] | 1186 ± 133 [1260] | 598 ± 126 [654] | <0.001 | 0.002 |
| $AUC_{ins\ 0-45\ min}$ (mU * min/L) | 2421 ± 245 [2132] | 2160 ± 195 [2327] | 1486 ± 216 [1458] | <0.001 | 0.010 |
| $AUC_{ins\ 0-60\ min}$ (mU * min/L) | 3476 ± 326 [3197] | 3081 ± 245 [3125] | 2505 ± 280 [2358] | 0.002 | 0.066 |
| $AUC_{ins\ 120-480\ min}$ (mU * min/L) | 4306 ± 499 [4356] | 5607 ± 900 [4808] | 5626 ± 557 [6034] | <0.001 | 0.047 |
| $T_{ins\ 50\%\ Late}$ (min) | 123.8 ± 10.5 [125.3] | 132.3 ± 18.7 [117.0] | 166.5 ± 10.6 [183.4] | 0.009 | 0.016 |
| $AUC_{ins\ 0-480\ min}$ (mU * min/L) | 10952 ± 889 [10465] | 11747 ± 1085 [11318] | 11694 ± 894 [12130] | 0.143 | 0.162 |
| $C_{max}$ (mU/L) | 83.8 ± 7.3 [86.2] | 76.0 ± 3.8 [76.9] | 74.7 ± 5.5 [77.0] | 0.123 | 0.828 |

Mean times to half maximal insulin concentrations ($T_{ins50\%Early}$), times to maximal insulin concentrations ($T_{insMax}$) and areas under the curve (AUC) for the first 30 and 45 minutes all indicated significantly increased early lispro absorption for both BIOD-238 and BIOD-250 compared to Humalog®. Mean times to half maximal concentration after the peak ($T_{ins50\%Late}$) and $AUC_{120-480min}$ indicated that BIOD-238 and BIOD-250 were associated with more rapid declines from peak concentrations relative to Humalog®. Table 15 summarizes injection site toleration data. The mean visual analog scale (VAS) score was numerically lower, but not significantly different for BIOD-250 compared to Humalog® (2.7±1.6 mm for BIOD-250 and 8.2±4.5 mm for Humalog®). The mean VAS score for BIOD-238 was significantly higher than that associated with Humalog® (24.2±7.0 mm, p=0.029 versus Humalog®). Assessments of absolute and relative injection discomfort severity scores mirrored VAS results (Table 15). General safety results were comparable between treatments.

TABLE 15

Injection Site Toleration Profiles of BIOD-238, BIOD-250 and HUMALOG®
Injection Site Toleration Profiles of BIOD-238, BIOD-250 and HUMALOG®

| Metrics | BIOD-238 N = 10 | BIOD-250 N = 11 | HUMALOG® N = 10 |
|---|---|---|---|
| Tolerability (VAS 0-100 mm) | 24.2 ± 7.0* (15.0) | 2.7 ± 1.6 (0.0) | 8.2 ± 4.5 (2.0) |
| Absolute Severity Score | 1.09 ± 0.2* (1.0) | 0.1 ± 0.1 (0.0) | 0.5 ± 0.2 (0.0) |
| Relative Severity Score | 3.6 ± 0.03 (4.0) | 2.9 ± 0.02 (3.0) | 3.2 ± 0.1 (3.0) |

Data represent the Mean ± SEM;
Median Values are presented in parentheses.
100 mm Visual Analog Scale (VAS): 0 = no discomfort, 100 = worst possible discomfort
Absolute Severity Scale: 0 = None, 1 = Mild, 2 = Moderate, 3 = Severe
Relative Severity (compared to usual meal-time insulin injections): 1 = Much less, 2 = Less, 3 = Equal, 4 = Increased, 5 = Greatly increased;
*p < 0.05 versus HUMALOG®

In conclusion, this study demonstrates that EDTA and citrate formulations of insulin lispro (both BIOD-238 and BIOD-250) have more rapid absorption rates and more rapid declines from peak concentrations compared to HUMALOG®. Furthermore, the presence of magnesium sulfate in BIOD-250 significantly mitigates local injection site discomfort without altering the ultra-rapid pharmacokinetic profile of BIOD-238.

The pharmacokinetics, pharmacodynamics and stability of BIOD 200 series formulations, when compared to a candidate target profile are shown in Table 16.

TABLE 16

Pharmacokinetic, Pharmacodynamic and Stability Characteristics of BIOD-238 & BIOD-250: Comparison to Candidate Target Product Profile

| Component | Metrics | Requirement |
|---|---|---|
| Tolerability | VAS (0-100 mm) Absolute Severity Score Relative Severity Score | Comparable injection site reactions versus Humalog® |

TABLE 16-continued

Pharmacokinetic, Pharmacodynamic and Stability
Characteristics of BIOD-238 & BIOD-250: Comparison to Candidate
Target Product Profile

| Component | Metrics | Requirement |
|---|---|---|
| Stability | Insulin Potency: 95.0-105.0%<br>HMWP: NMT 1.50%<br>A-21: NMT 1.50%<br>Total impurities (excluding A-21): NMT 4.0%<br>soluble and insoluble aggregates | Extrapolated stability results; 95% lower limit, to 18 (Minimum) to 24 months (Optimal) shelf life at 5° C. 14 (Minimum) to 28 (Optimal) day in-use dating for multiple daily injection; 95% lower limit at 25° C. for cartridges and vials 6-day (Minimum) in-use dating (to support label claim of 3 days, per FDA requirements) in a pump reservoir under thermo-mechanical stress; 95% lower limit; 37° C. |
| | soluble and insoluble aggregates | USP release specifications |
| "Rapid-On" Absorption Speed | $T_{ins\ 50\%\ Early}$ (min)<br>$T_{insMax}$ (min)<br>$AUC_{ins\ 0-30\ min}$ (mU * min/L) | 25%-40% improvement versus Humalog ® |
| Washout ("Tail") | $T_{ins\ 50\%\ Late}$ (min)<br>$AUC_{ins\ 120-480\ min}$ (MU * min/L) | Equivalent to or faster than Humalog ® |

Preclinical Studies in Diabetic Swine

Figure 10:
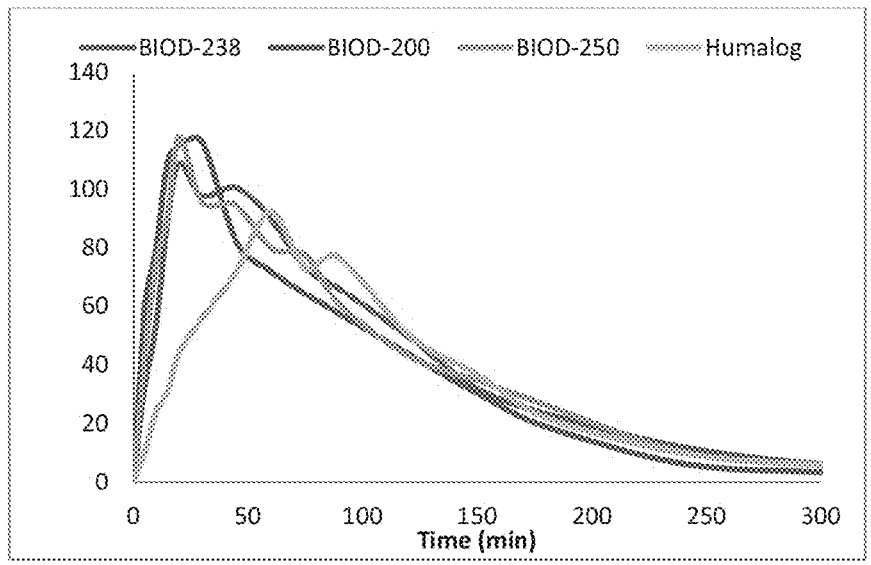
FIG. 10 shows the mean baseline subtracted insulin lispro versus time of HUMALOG®, BIOD-238, BIOD-200 and BIOD-250, 0-300 minutes post dose.
Figure 11:
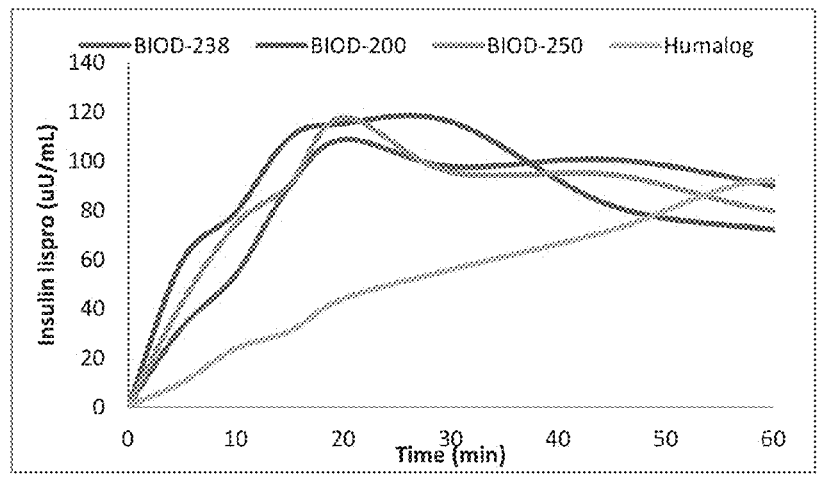
FIG. 11 shows the truncated mean baseline subtracted insulin lispro versus time of HUMALOG®, BIOD-238, BIOD-200, and BIOD-250, 0-60 minutes post dose.
Figure 12:
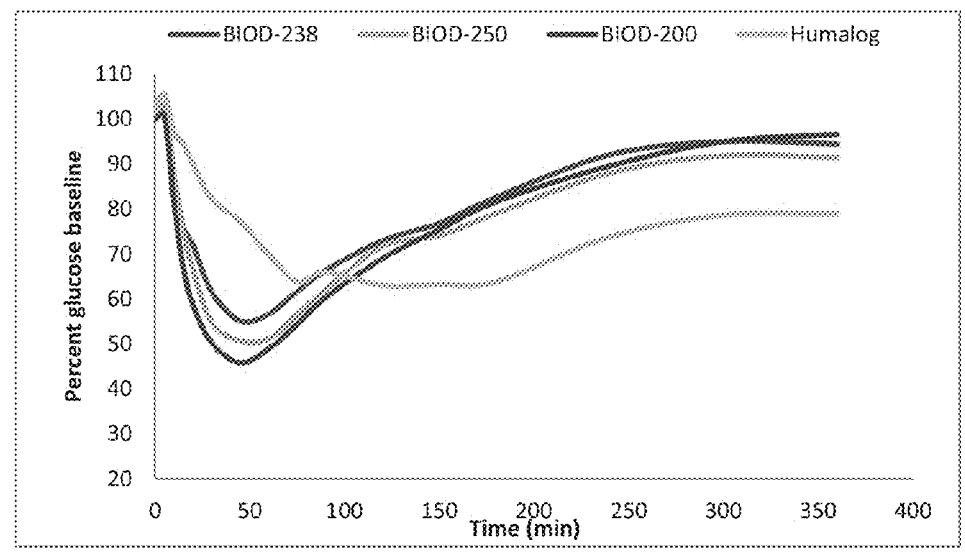
FIG. 12 shows the mean percent glucose lowering of the three test formulations BIOD-238, BIOD-250 and BIOD-200 in comparison to HUMALOG®.
Figure 13:
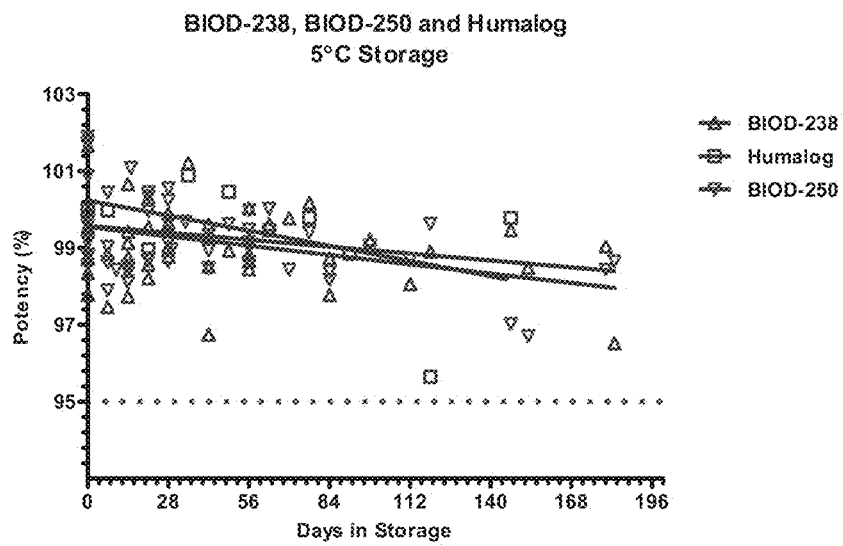
FIG. 13 shows insulin potency of BIOD-238, BIOD-250 and HUMALOG® at 5 C.
Figure 14:
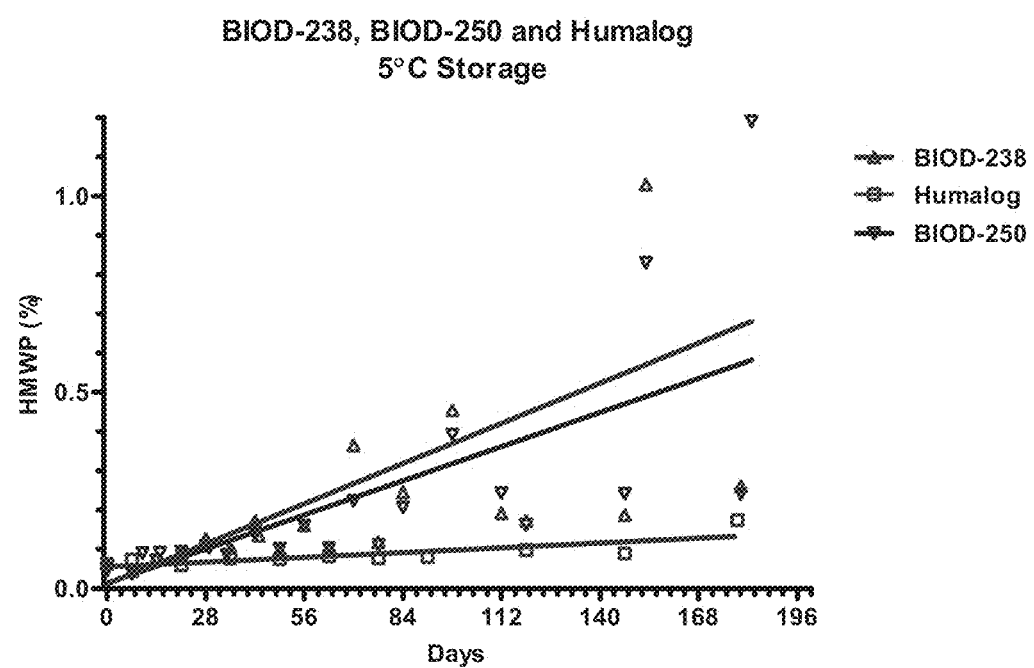
FIG. 14 shows high molecular weight protein (HMWP) plots of BIOD-238, BIOD-250 and HUMALOG® at 5° C.
Figure 15:
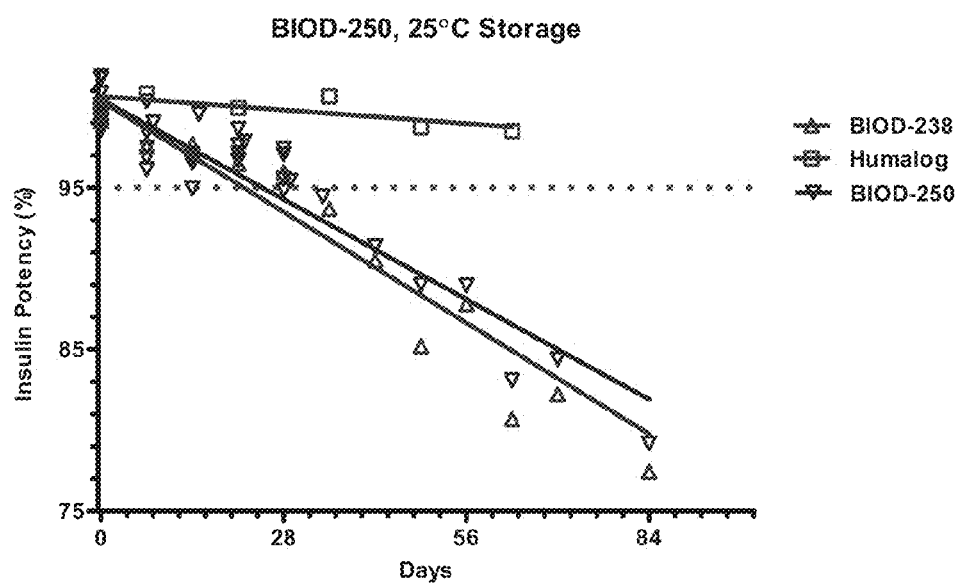
FIG. 15 show insulin potency plots of BIOD-238, BIOD-250 and Humalog® at 25° C.
Figure 16:
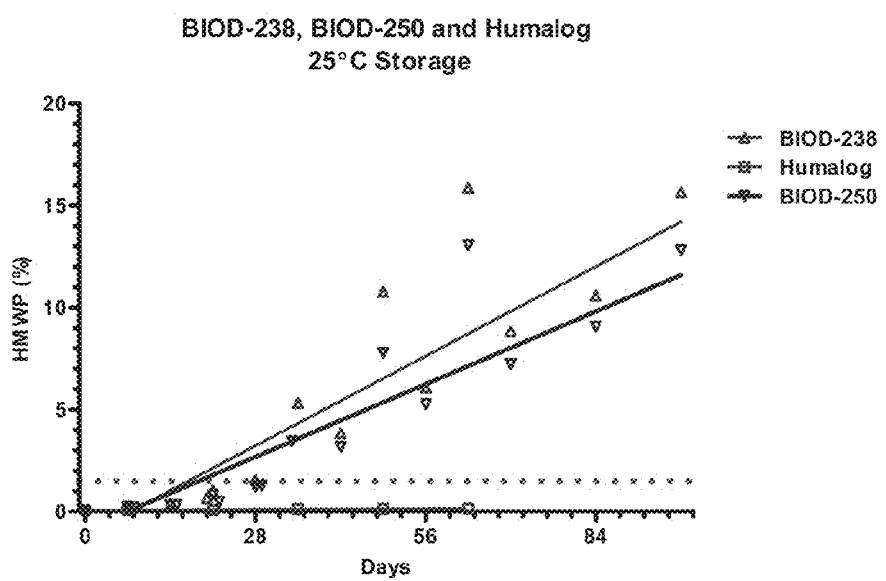
FIG. 16 shows high molecular weight protein (HMWP) plots of BIOD-238, BIOD-250 and HUMALOG® at 25° C.
Figures 17A, 17B:
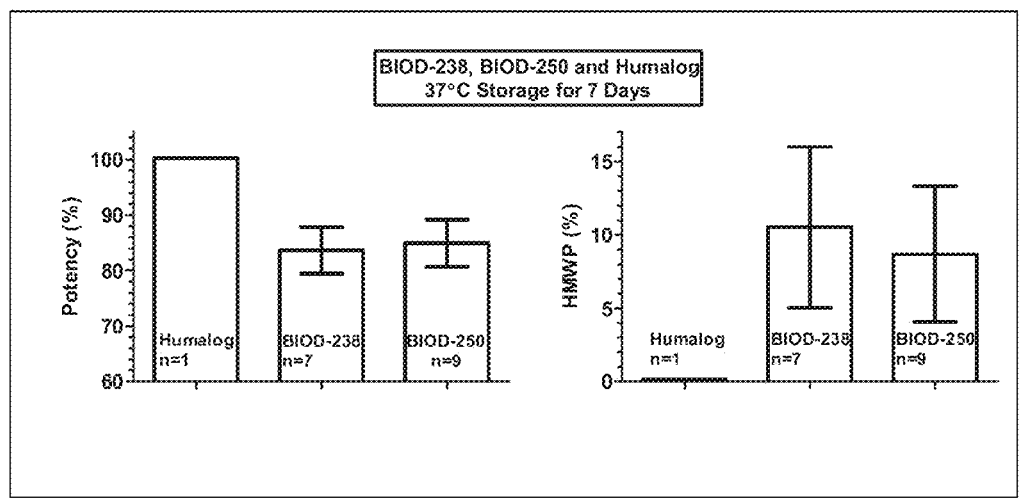
FIGS. 17A and 17B show insulin potency (17A) and high molecular weight protein (HMWP; 17B) for HUMALOG®, BIOD-238 and BIOD-250 stored at 37° C. for 7 days.
Figure 18A:
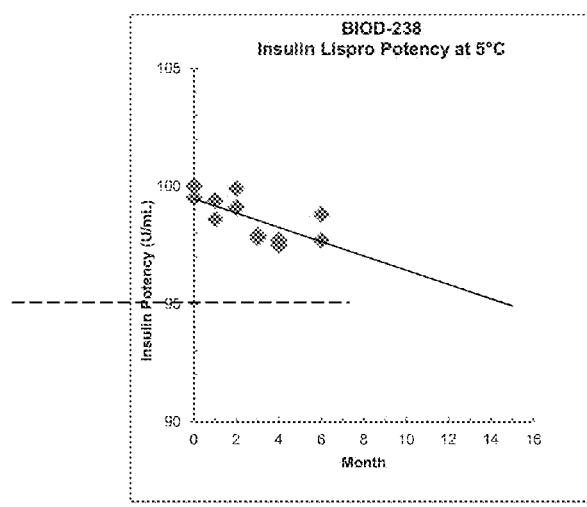
FIGS. 18A and 18B show insulin potency of BIOD-238 (manufactured under current good manufacturing practices (cGMP) from commercial preparations of HUMALOG®) at 5° C. (18A) and 25° C. (18B).
Figure 18B:
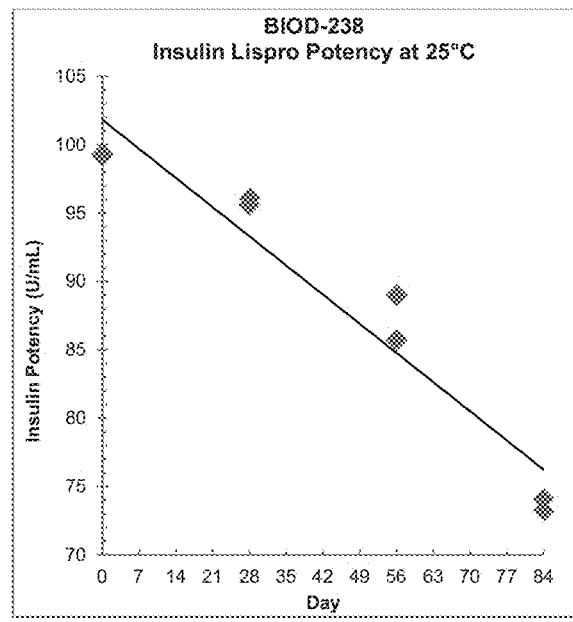
Figure 19A:
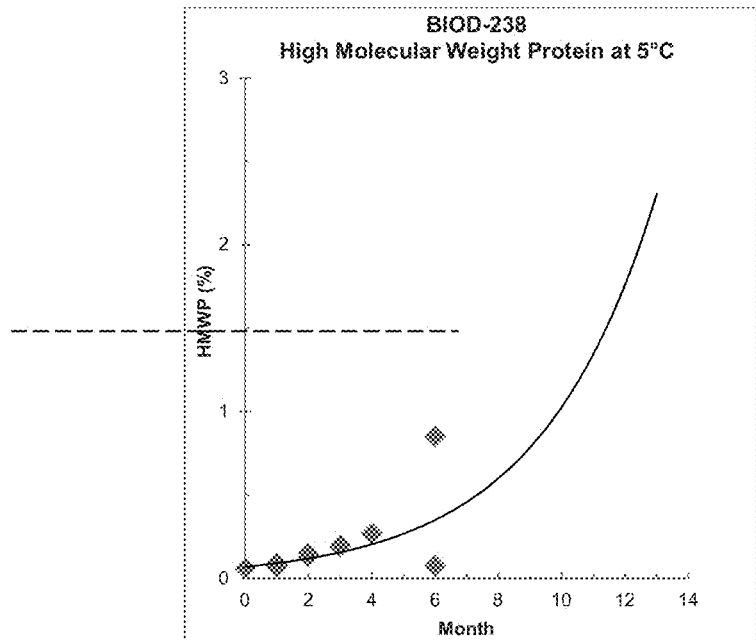
FIGS. 19A and 19B are plots of high molecular weight protein for BIOD-238 (manufactured under cGMP from commercial preparations of HUMALOG®) at 5° C. (19A) and 25° C. (19B).
Figure 19B:
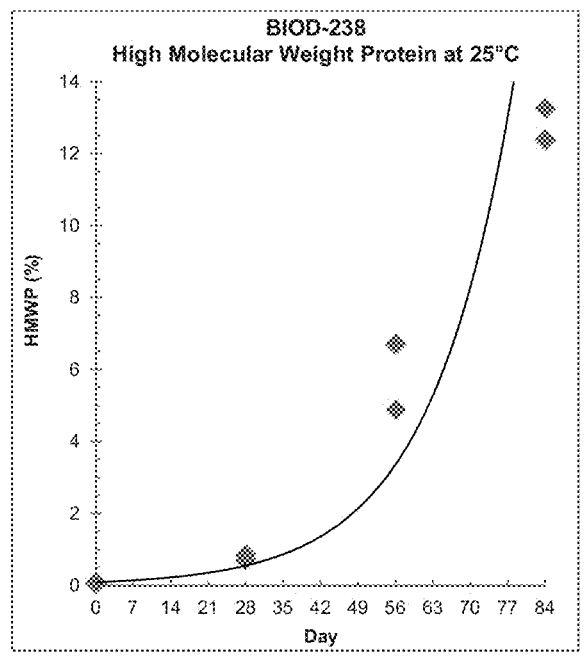
Figure 20A:
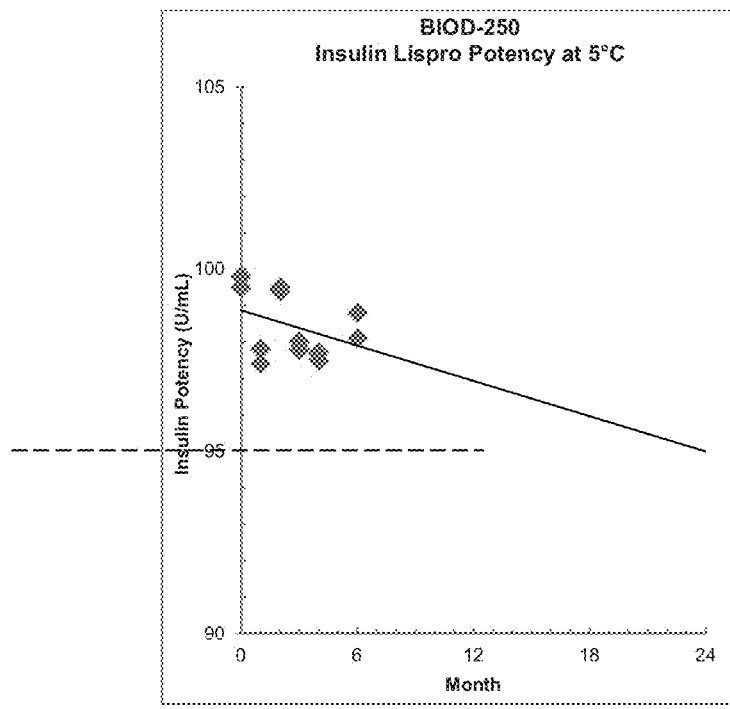
FIGS. 20A and 20B are graphs of Insulin potency of BIOD-250 (manufactured under cGMP from commercial preparations of HUMALOG®) at 5° C. (20A) and 25° C. (20B).
Figure 20B:
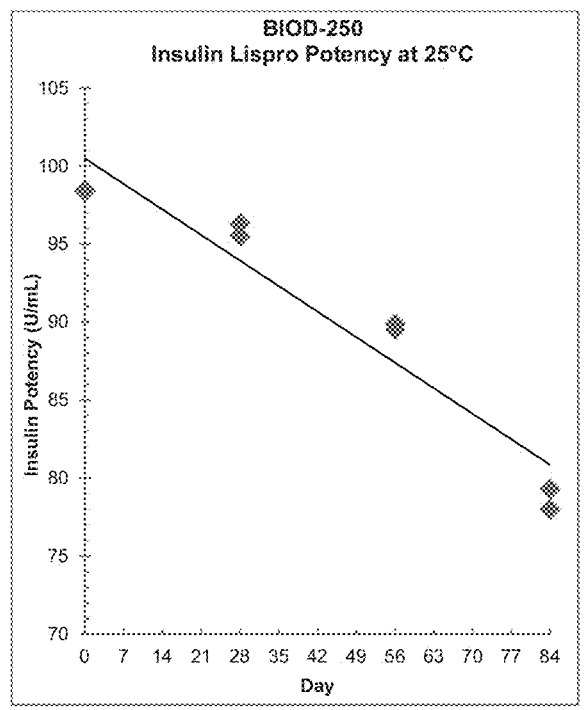
Figure 21A:
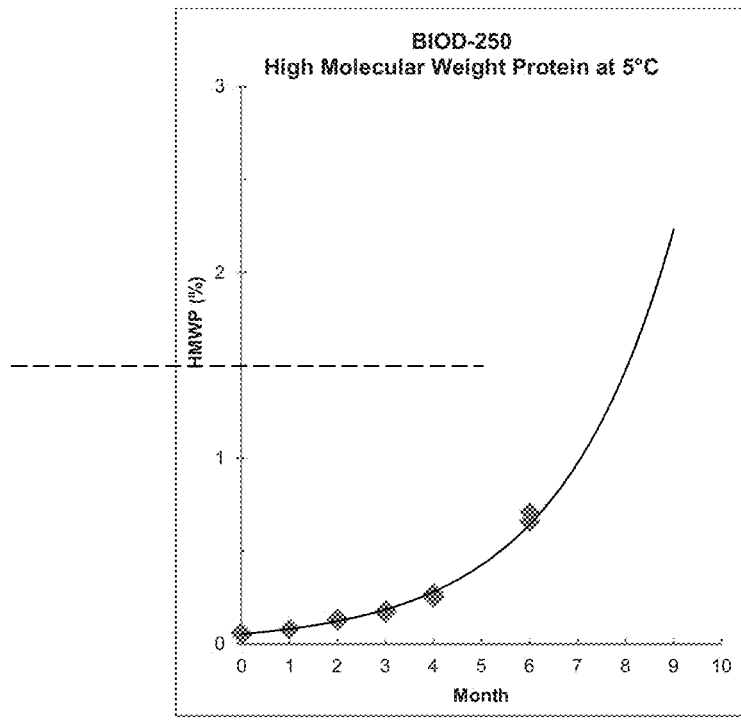
FIGS. 21A and 21B are graphs of high molecular weight protein of BIOD-250 (manufactured under cGMP from commercial preparations of HUMALOG®) at 5° C. (21A) and 25° C. (21B).
Figure 21B:
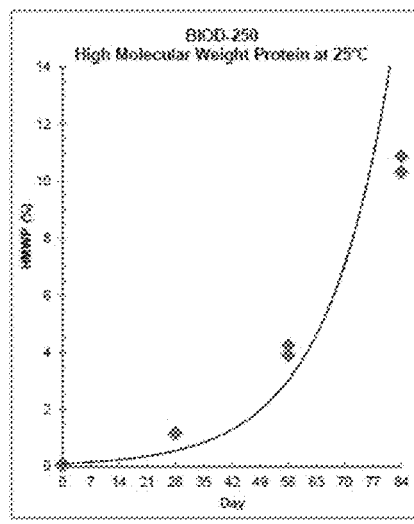

BIOD-200, BIOD-238 and BIOD-250, were tested in a three way randomized cross-over study in diabetic swine. The results were compared to a concurrent swine study of the marketed product, Humalog®. On each study day, a subcutaneous dose of 0.25 U/kg of each test drug was substituted for their daily bolus insulin dose and followed by a meal. Plasma insulin and glucose levels were monitored for 6 hours after dosing. The PK and PD profiles show that the formulations, BIOD-200, BIOD-238 and BIOD-250 have rapid absorption profiles in comparison with Humalog® (FIGS. 10-12 and Table 21). The PK timing parameters for BIOD-238 and BIOD-250 are not significantly different than BIOD-200. The timing of $T_{50\%max}$ and $T_{max}$ for all three formulations is significantly faster than Humalog® (see Table 17).

TABLE 17

Comparison of pharmacokinetic parameters of BIOD-238,
BIOD-250 and BIOD-200 versus Humalog ®

| PK Parameter | n = 9<br>BIOD-200 | n = 9<br>BIOD-238 | n = 9<br>BIOD-250 | n = 8<br>Humalog ® |
|---|---|---|---|---|
| $C_{max}$ (U/mL) | 136.2 ± 5.1 | 125.3 ± 20.0 | 121.7 ± 18.9 | 107.4 ± 17.8 |
| $T_{max}$ (min) | 20.6 ± 1.0**** | 27.8 ± 7.9*** | 23.9 ± 3.3**** | 69.4 ± 8.0 |
| $T_{50\%\ max}$ (min) | 7.9 ± 0.5*** | 10.1 ± 2.1* | 8.5 ± 1.4*** | 23.9 ± 4.7 |

Significant differences from Humalog ® at *p < 0.05, p < 0.01, *p < 0.005 & ****p < 0.001

Blood glucose data were analyzed using YSI 2300 STAT PLUS glucose analyzer with YSI 2710 turntable. Presented below are the blood glucose curves over time. All four formulations are compared. The blood glucose was normalized in FIG. 12 to remove variability of baseline glucose values.

The studies in diabetic swine demonstrate that the key excipients in Linjeta™ (Viaject™) formulations are active in modifying the pharmacokinetic profile of the insulin lispro-based formulations. The pharmacokinetic timing parameters for all three lispro-based formulations are significantly faster than Humalog® supporting an ultra-rapid absorption profile. The blood glucose lowering effect of the Biodel formulations also demonstrate an earlier and more robust effect.

EXAMPLE 5

The PK and PD of Rapid Acting Concentrated Insulin Formulation Compared to Commercial U-500 Formulation in Diabetic Miniature Swine The aim of the present study was to evaluate the pharmacokinetic (PK) and pharmacodynamic (PD) properties of a new U-400 concentrated insulin formulation designed for prandial use.

Methods and Materials

The composition of the formulation BIOD-530 was: 3.6 mg/ml EDTA, 1.8 mg/ml trisodium citrate, 2 mg/ml m-cresol, 16 mg/ml glycerin, 12.12 mg/ml insulin (400 U/mL).

Up to 10 diabetic miniature swine were injected in the morning with 0.25 U/kg of Lilly U-500R or BIOD-530, instead of their daily insulin. Animals were fed 500 g of swine diet directly after dosing and plasma samples were collected at −30, −20, −10, 0, 5, 10, 15, 20, 30, 45, 60, 75, 90, 120, 150, 180, 240, 300, 360, 420 and 480 min post dose using a Becton Dickinson $K_2$EDTA vacutainer. Frozen plasmas were assayed for insulin content (isoinsulin kit, Mercodia, USA) and analyzed for glucose concentration (YSI 3200 analyzer, YSI Life sciences, USA).

Figure 6:
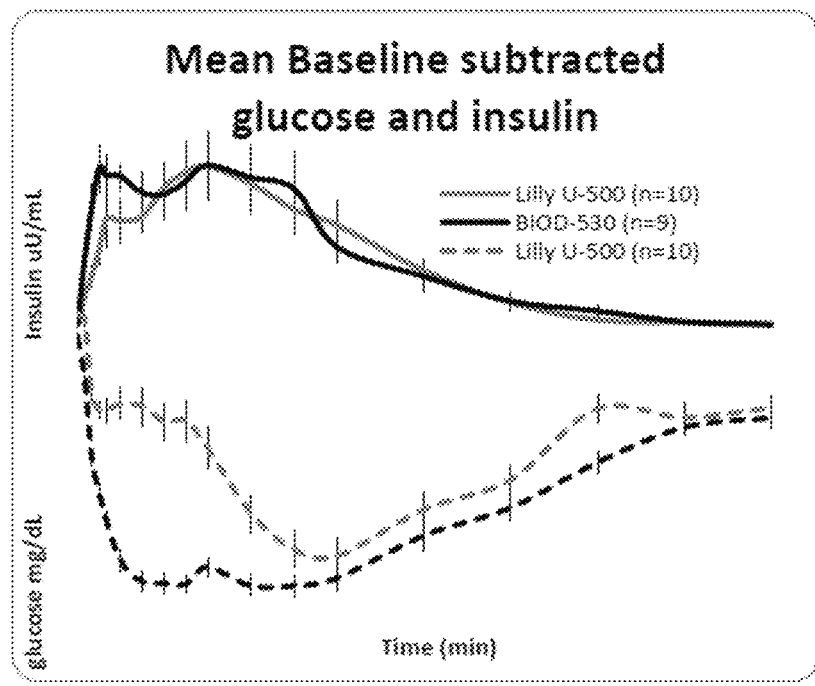
FIG. 6 shows the mean baseline subtracted insulin (solid lines) and glucose (dotted lines) versus time in diabetic miniature swine. BIOD-530 (black) and Lilly U-500 (grey), ±SEM.

Results:

The pharmacokinetic profile is shown graphically in FIG. 6, and calculated PK parameters are in Table 18.

TABLE 18

Calculated PK parameters:

|  | Lilly U-500 | BIOD-530 |
|---|---|---|
| Cmax | 135.5 ± 22.7 | 159.5 ± 18.7 |
| Tmax | 94 ± 17.1 | 41.7 ± 12.2* |
| $T_{1/2\ max}$ | 26.9 ± 5.0 | 11.1 ± 2.1* |

*p < 0.05

The pharmacodynamics are shown graphically as the mean of baseline subtracted glucose over time in FIG. 6.

Conclusion

The data shows the concentrated insulin formulation has a rapid action profile compared to the Lilly U-500 commercial formulation. The rapidity of the BIOD-530 formulation may be sufficient for prandial use.

EXAMPLE 6

Comparison of HUMALOG® (U-100) to BIOD-530 and BIOD-531 in Diabetic Miniature Swine The aim of the present study was to evaluate the pharmacokinetic (PK) and pharmacodynamic (PD) properties of a U-400 concentrated insulin formulation with Magnesium (BIOD-531) (TABLE 1) and a formulation without Magnesium (BIOD-530) (see Example 4) compared to HUMALOG®, a rapid acting U-100 analog insulin for prandial use.

Methods and Materials

The composition of the formulation BIOD-530 was: 3.6 mg/ml EDTA, 1.8 mg/ml trisodium citrate, 2 mg/ml m-cresol, 16 mg/ml glycerin, 12.12 mg/ml insulin (400 U/mL). BIOD-531 was the same composition as BIOD-530 with 4 mm Mg $SO_4$ added, intended to improve injection site tolerability.

Using a crossover study design, 9 diabetic miniature swine were injected in the morning with 0.25 U/kg of BIOD-530, BIOD-531 or HUMALOG® instead of their daily insulin. Animals were fed 500 g of swine diet directly after dosing and plasma samples were collected at −30, −20, −10, 0, 5, 10, 15, 20, 30, 45, 60, 75, 90, 120, 150, 180, 240, 300, 360, 420 and 480 min post dose using a Becton Dickinson $K_2$EDTA vacutainer. Frozen plasmas were assayed for insulin content (iso insulin kit, Mercodia) and analyzed for glucose concentration (YSI 3200 analyzer, YSI Life sciences, USA).

Figure 7A:
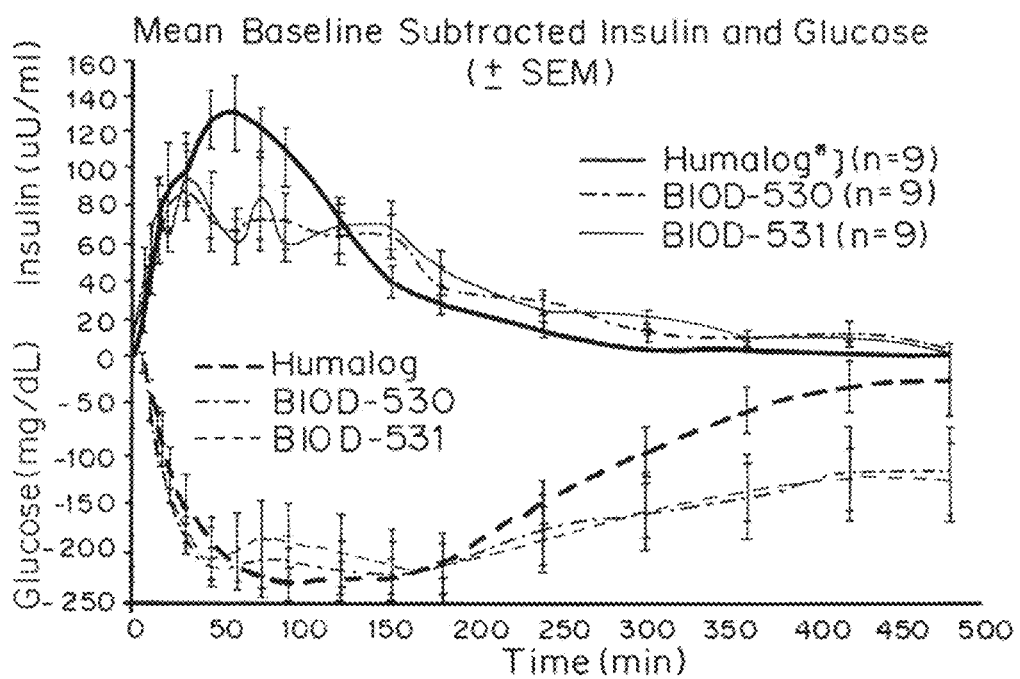
FIG. 7A is a graph of the mean baseline subtracted insulin (solid lines) and glucose lowering (dashed lines) of BIOD-530 (dark grey), BIOD-531 (light grey) and HUMALOG® (black) in diabetic swine. n=9, ±SEM.

Results:

Mean baseline subtracted insulin and glucose concentration versus time is shown in FIG. 7A. The pharmacokinetic parameters are in Table 19. The time to maximal concentration Tmax was similar across the formulations, while the time to half maximal concentration (½Tmax) trended earlier with the BIOD formulations.

TABLE 19

Pharmacokinetic Profiles of BIOD-530, BIOD-531 and HUMLOG ®

| Study 0.023 | HUMALOG ® | BIOD-530 | BIOD-531 |
|---|---|---|---|
| $C_{max}$ | 153 ± 14 | 108 ± 15 | 125 ± 16 |
| $T_{max}$ | 55 ± 7.5 | 67 ± 15 | 76 ± 16 |
| ½Tmax | 21 ± 4 | 9.6 ± 1.4 | 11 ± 9 |
| AUC | 16656 ± 1440 | 16508 ± 2482 | 17724 ± 2293 |

Conclusion: The addition of Magnesium to the formulation did not alter the pharmacokinetic or pharmacodynamic profile of BIOD-530. In addition, both the concentrated formulation, BIOD-530 and 531 were at least as rapid absorbing as HUMALOG®, and had a slightly faster onset of action than HUMALOG®. The total duration of action the U-400 formulations was longer than HUMALOG®.

EXAMPLE 7

Reduction of Disodium EDTA and Loss of Rapid Absorption in Diabetic Miniature Swine The purpose of this study was to find the lowest EDTA concentration that was effective in maintaining an ultra-rapid absorption pharmacokinetic profile. Two formulations were made with successively less EDTA concentration than BIOD-530.

BIOD-532 had 2.7 mg/ml disodium EDTA and BIOD-533 had 1.8 mg/ml disodium EDTA. The rest of the components remained the same composition as BIOD-530 (See Example 4).

Using a crossover study design, 9 diabetic miniature swine were injected in the morning with 0.25 U/kg of BIOD-530, BIOD-532 or BIOD-533 instead of their daily insulin. Animals were fed 500 g of swine diet directly after dosing and plasma samples were collected at −30, −20, −10, 0, 5, 10, 15, 20, 30, 45, 60, 75, 90, 120, 150, 180, 240, 300, 360, 420 and 480 min post dose using a Becton Dickinson $K_2$EDTA vacutainer. Frozen plasmas were assayed for insulin content (iso insulin kit, Mercodia) and analyzed for glucose concentration (YSI 3200 analyzer, YSI Life sciences, USA).

Figure 8:
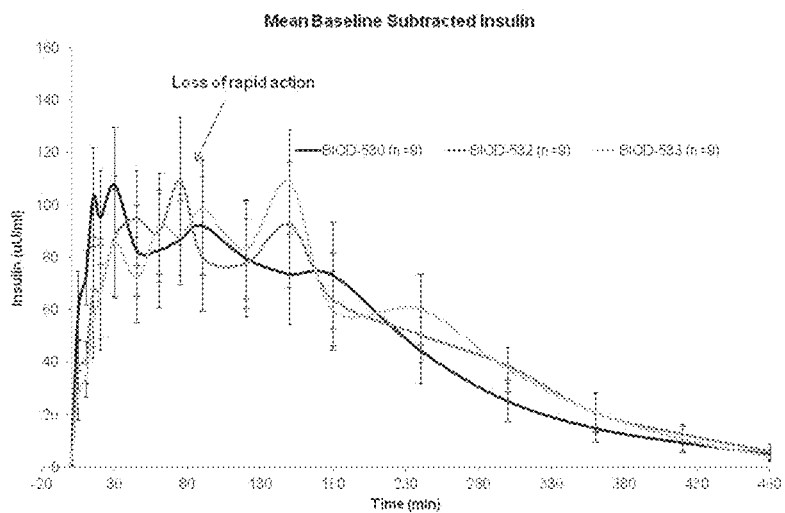
FIG. 8 shows the mean baseline subtracted insulin concentration versus time of BIOD-530 (black), BIOD-532 (dark grey) and BIOD-533 (light grey) in miniature diabetic swine. n=9, ±SEM.

Results: The concentration versus time profile is shown in FIG. 8 and pharmacokinetic parameters in Table 20. Though the AUC and Cmax were consistent across the formulations, the early onset of absorption was lost as less EDTA was added.

TABLE 20

Pharmacokinetic Profiles of BIOD-530, BIOD-532 and BIOD 533

|  | BIOD-530 | BIOD-532 | BIOD-533 |
|---|---|---|---|
| $C_{max}$ | 137.7 ± 17.8 | 139 ± 21 | 145 ± 21 |
| $T_{max}$ | 36.1 ± 9.3 | 58.9 ± 11.8 | 103 ± 28 |
| ½Tmax | 10.3 ± 2.8 | 21.5 ± 4.6* | 29 ± 7* |
| AUC | 22674 ± 4585 | 24102 ± 4573 | 24427 ± 3830 |

Conclusion: In order to maintain the rapid onset of insulin absorption, greater than 2.7 mg/mL of disodium EDTA must be used.

EXAMPLE 8

A Novel Concentrated Recombinant Human Insulin Formulation with Improved Ultra-Rapid Prandial and Similar Basal Absorption as Insulin Lispro Protamine Mixes Background and Aims: Formulations of U-100 recombinant human insulin (RHI) and insulin lispro (IL) containing EDTA and citrate show increased rates of absorption after subcutaneous (sc) injection in man compared to commercial formulations of RHI and IL. BIOD-530 and BIOD-531 are similar EDTA/citrate formulations with RHI concentrations of 400 U/ml. In previous studies in diabetic pigs, BIOD-530 had a significantly faster onset and similar duration of action to RHI U-500 which provides both prandial and basal coverage in type 2 diabetes patients requiring larger injection volumes. BIOD-531 was developed with MgSO$_4$ to mitigate EDTA related injection site discomfort. The aim of this study was to compare pharmacokinetic (PK) and pharmacodynamic (PD) profiles in diabetic miniature swine of BIOD-531 with U-100 formulations of mixtures of IL-Protamine (ILP) and IL 50/50 (ILP/IL 50/50) and 75/25 (ILP/IL 75/25) which also provide both prandial and basal coverage in patients with diabetes.

Materials and Methods: Test formulations consisted of ILP/IL 75/25, ILP/IL 50/50 and BIOD-531. On the morning of each crossover study, miniature diabetic swine were given a sc dose (0.25 U/kg) of test formulation followed by a meal. Study 1 and Study 2 compared BIOD-531 with ILP/IL 75/25 and ILP/IL 50/50, respectively. Blood glucose and plasma insulin were sampled from −30 to 480 min post dose. Plasma insulin was measured by an ELISA method and glucose concentration determined by YSI. Time to half maximal concentration ($T_{50\% \, early}$) was calculated for each swine and averaged for each test article. Results of each study compared BIOD-531 to ILP/IL 75/25 or 50/50 mixtures using Students t-test.

Figure 9:
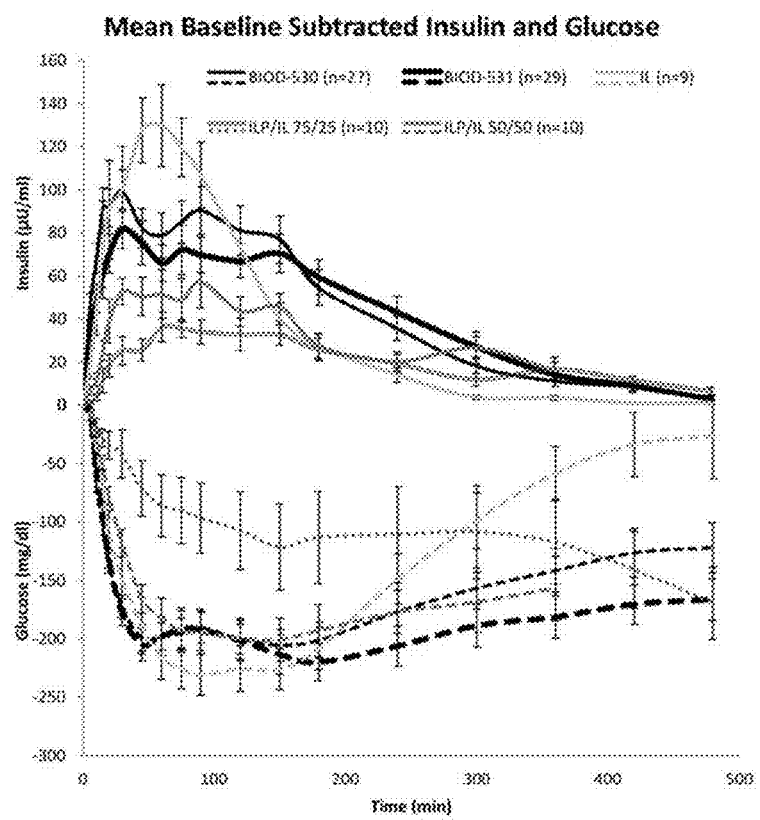
FIG. 9 shows the mean baseline subtracted insulin (solid lines) and glucose (dotted lines) versus time in diabetic miniature swine following administration of different insulin formulations.

Results: Concentration versus time profiles are shown in FIG. 9; data for BIOD-530 and IL are included as a reference. Insulin concentration rose to higher peaks after BIOD-531 injection compared to either ILP/IL mixture. Despite rising to a higher peak, the absorption rates as reflected by $T_{50\%early}$ (min) and $AUC_{0-30min}$ (µU/ml*min) of BIOD-531 (Study 1:25±5 and 1582±397; Study 2: 11±2 and 1475±134, respectively) were more rapid than ILP/IL 75/25 (35±6 and 351±82*, respectively) or ILP/IL 50/50 (23±3* and 777±128*, respectively) and resulted in a more rapid decline of glucose concentrations (*p<0.05 versus BIOD-531). The duration of action as reflected by the percent total $AUC_{150-480min}$ was similar across the formulations: BIOD-531 (32-43%), ILP/IL 75/25 (45%) and ILP/IL 50/50 (35%). The glucose concentrations of all three formulations remained suppressed up to 480 min while insulin and glucose concentrations returned towards baseline levels around 240 min following IL administration.

Conclusion: BIOD-531 has a rapid onset of action comparable to IL and a similar basal control profile to ILP/IL pre-mixed insulins. BIOD-531 should provide deliver improved prandial and comparable basal coverage as pre-mixed insulins with lower injection volumes. The calcium EDTA based insulin formulations showed a lack of enhanced stability with Calcium and Magnesium and reduced onset of absorption when calcium is present in the formulation. When compared to a U-400 formulation without $MgSO_4$ (BIOD-530), there was no difference in the rate of rapid absorption, instead both formulations were absorbed equally well.

TABLE 21

Comparisons of Calcium disodium EDTA (BIOD-548), disodium EDTA(BIOD-530) and disodium EDTA with $MgSO_4$(BIOD-531) in U-400 regular human insulin formulations:

|  | BIOD-548 | BIOD-531 | BIOD-530 |
|---|---|---|---|
| $Na_2$ EDTA | — | 3.60 mg/ml (9.67 mM) | 3.60 mg/ml (9.67 mM) |
| $CaNa_2EDTA$ | 3.62 mg/ml (9.67 mM) | — | — |
| Trisodium Citrate | 1.8 mg/ml | 1.8 mg/ml | 1.8 mg/ml |
| m-cresol | 2 mg/ml | 2 mg/ml | 2 mg/ml |
| glycerin | 16 mg/ml | 16 mg/ml | 16 mg/ml |
| Insulin | 15.12 mg/ml | 15.12 mg/ml | 15.12 mg/ml |
| $MgSO_4$ |  | 4 mM |  |
| pH | 7.5 | 7.5 | 7.5 |

Figure 7B:
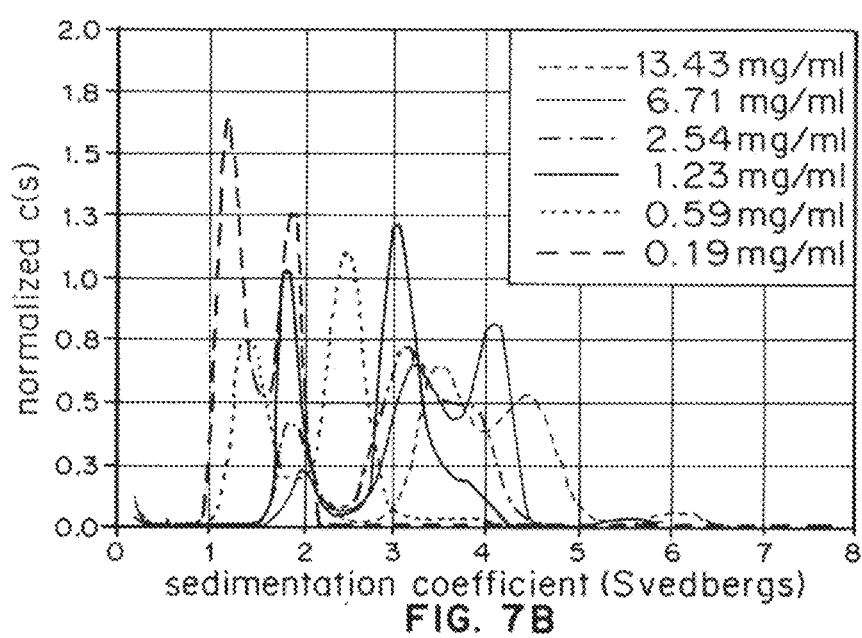
FIGS. 7B and C show Analytical ultracentrifugation as a graphic illustration plotting normalized continuous sedimentation coefficient c(s) versus sedimentation coefficient.
Figure 7C:
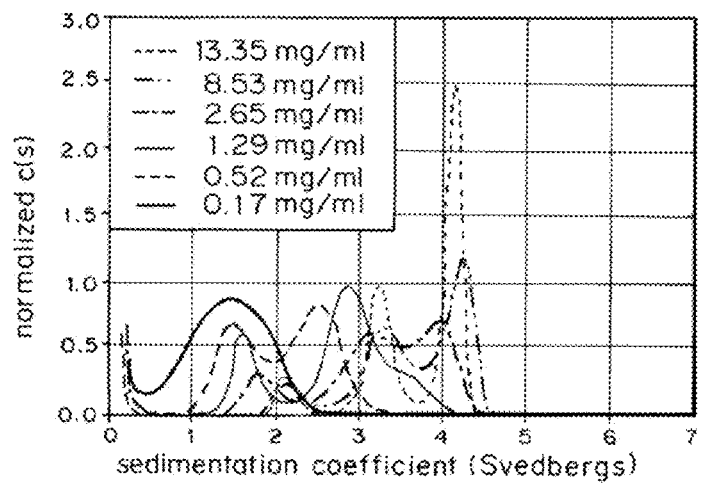
FIG. 7D shows similar analysis of HUMULIN® U-500 undergoing analytical ultracentrifugation.
FIG. 7E shows Mean baseline subtracted insulin concentration versus time in miniature diabetic swine, comparing formulations with (BIOD-548) and without calcium (BIOD-531) compared to HUMULIN® U-500. The rapid onset of action demonstrated with BIOD-531 is missing with the calcium EDTA formulation. +/−SEM.
FIG. 7F shows potency at 14 days at 37° C. of different lots and formulations. BIOD-531 and 530 are identified, verifying there is no improvement in the stability upon addition of MgSO4 to the formulation.
Figure 7D:
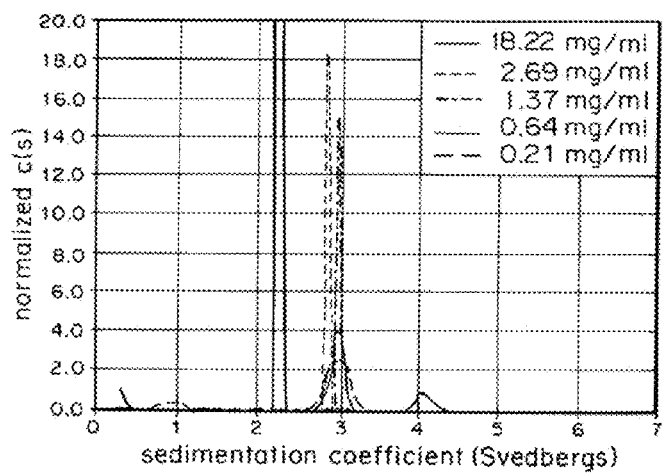

Analytical Ultracentrifugation is used to examine insulin size. A left shift toward smaller insulin forms follows dilution in formulation diluent. A Svedburg of 3 is associated with hexameric insulin while ~1 is a monomer. The concentrated insulin is centrifuged undiluted as well as diluted with its own diluent (exact formulation composition without insulin). As shown in FIGS. 7B and C (BIOD-548), though both formulations show polydisperse insulin forms at all concentrations, the left side appears more efficient in shifting to smaller monomeric forms on dilution. This indicates very rapid onset of insulin action on injection. FIG. 7D (Humulin R U-500) shows that there is a very small amount of insulin shifting to the smaller sized monomer/dimers on dilution. Note the highest concentration looks somewhat small, however it is a more stable compact hexamer which resolves to 3 (S) on dilution (hexamer). There is very little movement towards the smaller sized monomers and dimers, so it is expected that this formulation will be slower to absorb than the BIOD formulations.

Figure 7E:
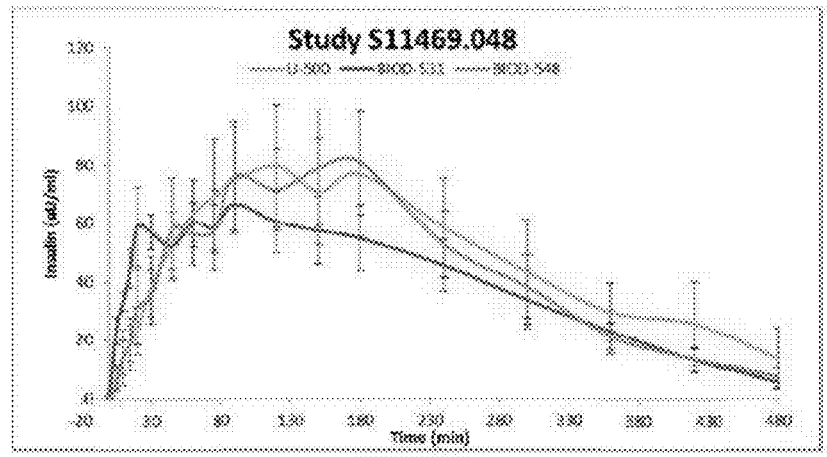

The absorption of insulin following administration of these formulations in diabetic swine is shown in FIG. 7E. A comparison of the PK parameters for U-500, BIOD-*531 and BIOD-548 is shown in Table 22.

TABLE 22

PK parameters of the formulations show the rapid onset of action, as shown by Tmax and T50% max are lost when Calcium EDTA is in the formulation.

|  | U-500 | BIOD-531 | BIOD-548 |
|---|---|---|---|
| Cmax | 101 ± 21 | 93 ± 12 | 103 ± 19 |
| Tmax | 115 ± 20 | 71 ± 17 | 135 ± 18 |
| $T_{50\% \, max}$ | 39 ± 7 | 17 ± 16* | 42 ± 8 |

Stability of the Formulation

TABLE 23

Visual observations of formulations following incubation under stressed conditions

| Days at 37 C. | 37 C.-static | | 37 C.-Agitation | |
|---|---|---|---|---|
|  | BIOD-548 | BIOD-531 | BIOD-548 | BIOD-531 |
| 0 | clear | clear | clear | clear |
| 7 | clear | clear | clear | clear |
| 14 | clear | clear | clear with fibril | clear |

TABLE 24

High Molecular weight by HPLC following incubation under stressed conditions
HMWP (%) at 37 C.

| | 37° C.-static | | 37° C.-Agitation | |
|---|---|---|---|---|
| Days at 37° C. | BIOD-548 | BIOD-531 | BIOD-548 | BIOD-531 |
| 0 | 0.29 | 0.28 | 0.29 | 0.28 |
| 7 | 0.59 | 0.5 | 0.67 | 0.54 |
| 14 | 1.2 | 0.72 | 1.68 | 0.9 |
| 21 | 2.08 | 1.28 | | |

Figure 7F:
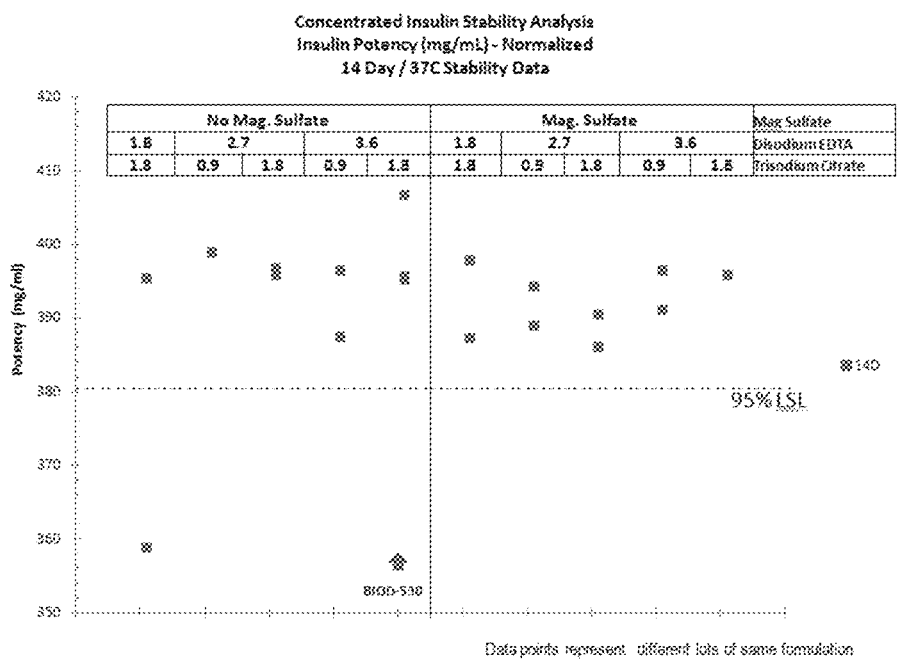

The calcium EDTA formulation, which according to the literature should have enhanced insulin stability, shows considerably higher HMWP compared to BIOD-531. FIG. 7F compares the stability of BIOD-531 to BIOD-530, which are identical formulations except for the addition of $MgSO4$. Unexpectedly, there is no advantage in stability upon the addition of Magnesium to the formulation. FIG. 7F shows potency at 14 days at 37° C. of different lots and formulations. BIOD-531 and 530 are identified, verifying there is no improvement in the stability upon addition of MgSO4 to the formulation.

In Summary:

The addition of Calcium EDTA to insulin rapidly reduces the size of insulin, making it readily available for absorption.

When administered to swine, there is no benefit to the reduced insulin size, instead it is slowly absorbed at a rate similar to Humulin R U-500.

The stability of the formulation containing calcium has more "high molecular weight" protein than the identical formulation without calcium under stressed conditions.

There is no advantage to adding magnesium or calcium to our formulations to improve stability. In addition, calcium reduces the rate of insulin absorption, likely due to negation of the charge masking effect of citrate. Magnesium's role in this formulation appears to be specifically for improvement in injection site tolerability. It does not appear to interfere with sodium citrate in solution and its addition to the formulation does not change the formulations rapid rate of insulin absorption.

EXAMPLE 9

Stability Studies for Ultra-rapid Acting Insulin Lispro Formulations

Materials and Methods

Multiple lots of BIOD-238 (n=9) and BIOD-250 (n=11) were produced for stability evaluation. The control material consisted of aliquots of pooled HUMALOG® (5 lots) in 5 mL vials. The formulations were packaged in cartridges or vials and stored at 5° C., 25° C. and 37° C. The materials were sampled at various time points for insulin potency using RP-HPLC and HMWP using SEC-HPLC. The data were compiled into tables and graphed.

The shelf-life estimates based on insulin potency for BIOD-238, BIOD-250 and HUMALOG® are 711 days, 524 days and 373 days, respectively. However, HMWP is the limiting factor with HMWP approaching the allowable limits of 1.5% at 6 months. Real-time data was used to make projections at 25° C. and 37° C. since the degradation is within the timeframe of the experimental measurements. The shelf life for BIOD-238 and BIOD-250 at 25° C. is around 28 days and at 37° C. is less than 7 days.

The addition of the excipients discussed above to commercial preparations of Humalog® produces ultra-rapid-acting insulins. The stability profiles of BIOD-238 and BIOD-250 at all the temperatures examined are inferior to HUMALOG®. The generation of HMWP (rather than insulin potency) appears to be the rate-limiting step with regards to determination of the shelf life of the formulations. These data are in keeping with the physical characterization studies described below.

GMP Manufactured Lot

The clinical batches of BIOD-238 and BIOD-250 were manufactured under GMP at the University of Iowa Pharmaceuticals (location: Iowa City, Iowa). Each product formulation used commercial Humalog® and was bulk compounded with Biodel's excipients then filled into 5 mL vials and release tested for clinical use. There was no process development done to optimize the stability of the formulation since the shelf life was only required to cover the timeframe of the Phase 1 clinical study (a few months at 5° C.).

FIGS. 18A-21B graphically present the Insulin Lispro Potency (using test method T0114) and High Molecular Weight Protein stability data for BIOD-238 (FIGS. 18A-19B) and BIOD-250 (FIGS. 20A-21B) at 5° C. (18A, 19A, 20A, 21A) and 25° C. (18B, 19B, 20B, 21B). The data are summarized in Table 25.

TABLE 25

| Test | USP Spec | 0 mo | 6 mo*, 5° C. | 1 mo, 25° C. | 2 mo, 25° C. | 3 mo, 25° C. |
|---|---|---|---|---|---|---|
| | | BIOD-238, lot number 071I0712 | | | | |
| Insulin lispro | 95.0-105.0% | 99.3, 99.2 | 97.7, 98.0 | 96.1, 96.6 | 88.7, 89.0 | 73.2, 74.1 |
| % Related compounds** | NMT 4.00% | 0.33, 0.32 | 2.53, 2.45 | 4.58, 4.84 | 16.4, 11.9 | 27.09, 26.47 |
| HMWP | NMT 1.50% | 0.06, 0.06 | 0.76, 0.85 | 0.71, 0.85 | 6.70, 4.88 | 13.25, 12.83 |
| Appearance | Clear, colorless solution essentially particle free | Clear, colorless solution essentially particle free | Clear, colorless solution essentially particle free | Clear, colorless solution essentially particle free | Clear, colorless solution with particles | Clear, colorless solution with particles |
| Particle Matter | < or = 6000 particles per container (> or = 10 mm) | 3116 | n/a | n/a | n/a | n/a |
| | < or = 6000 particles per container (> or = 25 mm) | 84 | n/a | n/a | n/a | n/a |
| | | BIOD-250, lot number 072I0712 | | | | |
| Insulin lispro | 95.0-105.0% | 98.4, 98.4 | 98.8, 98.1 | 95.5, 96.3 | 89.9, 89.5 | 78.0, 79.3 |
| % Related compounds** | NMT 4.00% | 0.30, 0.30 | 2.33, 2.42 | 4.49, 4.64 | 10.63, 11.01 | 23.96, 22.67 |
| HMWP | NMT 1.50% | 0.05, 0.06 | 0.66, 0.71 | 1.16, 1.17 | 3.92, 4.26 | 10.88, 10.31 |
| Appearance | Clear, colorless solution essentially particle free | Clear, colorless solution essentially particle free | Clear, colorless solution essentially particle free | Clear, colorless solution essentially particle free | Clear, colorless solution with particles | Clear, colorless solution with particles |
| Particle Matter | < or = 6000 particles per container (> or = 10 mm) | 2017 | n/a | n/a | n/a | n/a |
| | < or = 6000 particles per container (> or = 25 mm) | 20 | n/a | n/a | n/a | n/a |

*Note:
6 Month Insulin lispro Potency results from Biodel's "In-House" Test Method
**Related compounds have not been characterized Based on the stability data shown in the figures discussed above, the shelf life projections have been estimated and summarized in Table 26 below.

A summary of the PK and stability characteristics of BIOD-238 and BIOD-250 are compared with the candidate target product profile in Table 27.

TABLE 26

Shelf life projections based on stability data of BIOD-238 and BIOD-250 made from commercial preparations of Humalog ®

|  | BIOD-238 | | BIOD-250 | |
| --- | --- | --- | --- | --- |
|  | 5 C. | 25 C. | 5 C. | 25 C. |
| Insulin Potency | 14 months | 22 days | 23 months | 23 days |
| HMWP | 11 months | 43 days | 8 months | 44 days |

TABLE 27

Summary of the PK and Stability Characteristics of BIOD-238 & BIOD-250 in Comparison with the Candidate Target Product Profile

| Target Product Profile | Parameter | Humalog ® | BIOD-238 | BIOD-250 |
| --- | --- | --- | --- | --- |
| Comparable injection site reaction versus Humalog ® | VAS (0-100 mm) | 8.2 ± 4.5 | 242 ± 7.0 (p < 0.05) | 2.7 ± 1.6 |
|  | Absolute Severity Score | 0.5 ± 0.2 | 1.1 ± 0.2 | 0.1 ± 0.1 |
|  | Relative Severity Score | 3.2 ± 0.1 | 3.6 ± 0.3 | 2.9 ± 0.2 |
| Chemical Stability (Insulin Potency: >95%; HMWP: <1.5%) | Extrapolated stability results to 18 (Minimum) to 24 months (Optimal) shelf life at 5° C. |  | Based on Clinical Lot: Insulin Potency: 14 months HMWP: 11 months Based on Research Lots: Insulin Potency: 23.7 months HMWP: 6.5 months | Based on Clinical Lot: Insulin Potency: 23 months HMWP: 8 months Based on Research Lots: Insulin Potency: 17.5 months HMWP: 6.5 months |
|  | 14 (Minimum) to 28 (Optimal) day in-use dating for multiple daily injection at 25° C. for cartridges and vials |  | Based on Clinical Lot: Insulin Potency: 22 days HMWP: 43 days Based on Research Lots: Insulin Potency: 28 days HMWP: 20 days | Based on Clinical Lot: Insulin Potency: 23 days HMWP: 44 days Based on Research Lots: Insulin Potency: 28 days HMWP: 28 days |
|  | 6 (Minimum) to 14 (Optimum) day in-use dating in a pump reservoir under thermo-mechanical stress; 37° C. |  | Based on Research Lots: Insulin Potency: <7 days HMWP: <7 days | Based on Research Lots: Insulin Potency: <7 days HMWP: <7 days |
| Physical Characteristics (Levels of soluble and insoluble aggregates in each formulaaation as well as aubvisible particulates) | USP Release Specifications: < or = 6000 particles per container (> or = 10 um) |  | 3116 | 2017 |
|  | < or = 600 particles per container (> or = 25 um) |  | 84 | 20 |
| "Rapid-On" Absorption Speed (25%-40% improvement versus Humalog ®) | Clinical Studies: $T_{ins\,50\%\,Early}$ (min) | 24.8 ± 2.9 | 13.7 ± 1.9 (p < 0.001) | 14.6 ± 1.9 (p = 0.001) |
|  | $T_{insMax}$ (min) | 62.5 ± 8.4 | 35.5 ± 2.5 (p = 0.013) | 40.9 ± 6.1 (p = 0.025) |
|  | $AUC_{ins\,0\text{-}30\,min}$ (mU * min/L) Diabetic Swine | 598 ± 126 | 1278 ± 164 (p < 0.001) | 1278 ± 133 (p = 0.002) |

TABLE 27-continued

Summary of the PK and Stability Characteristics of BIOD-238 & BIOD-250 in Comparison with the Candidate Target Product Profile

| Target Product Profile | Parameter | Humalog ® | BIOD-238 | BIOD-250 |
|---|---|---|---|---|
| | Studies: | | | |
| | $T_{ins\ 50\%\ Early}$ (min) | 23.9 ± 4.7 | 10.1 ± 2.1 (p < 0.05) | 8.5 ± 1.4 (p = 0.005) |
| | $T_{insMax}$ (min) | 69.4 ± 8.0 | 27.8 ± 7.9 (p < 0.005) | 23.9 ± 3.3 (p < 0.001) |
| | $AUC_{ins\ 0-30\ min}$ (mU*min/L) | 937.0 ± 156.4 | 2186.1 ± 252.7 (p < 0.001) | 2399.2 ± 366.3 (p = 0.003) |
| Washout ("Tail") Equivalent to or faster than Humalog ®) | Clinical Studies: $T_{ins\ 50\%\ Late}$ (min) | 166.5 ± 10.6 | 123.8 ± 10.5 (p = 0.009) | 132.3 ± 18.7 (p = 0.016) |
| | $AUC_{ins\ 120-480\ min}$ (mU * min/L) Diabetic Swine Studies: | 5626 ± 577 | 4306 ± 499 (p < 0.001) | 5607 ± 900 (p = 0.047)) |
| | $T_{ins\ 50\%\ Late}$ (min) | 126.2 ± 10.5 | 93.3 ± 11.2 (p = 0.05) | 93.5 ± 7.8 (p = 0.02) |
| | $AUC_{ins\ 120-360\ min}$ (mU * min/L) | 3937.6 ± 712.0 | 3960.5 ± 1238.7 | 3933.9 ± 1163.1 |

Significant pharmacokinetic and injection site tolerability differences of BIOD-238 or BIOD-250 versus Humalog® are shown in parentheses. The stability data presented are for formulations that were made using commercial preparations of Humalog® and have not been further optimized for stability in process development studies.

Physical Characterization of BIOD-238 and BIOD-250: Comparison to HUMALOG®, RHI and RHI-based Ultra-rapid-acting Formulations To physically characterize the ultra-rapid-acting formulations, several techniques have been used including dynamic light scattering ("Malvern"), size exclusion chromatography and analytical ultracentrifugation. The size characterization of the insulin was detailed in a study focused on the chemical and physical stability of BIOD-238, BIOD-250 and HUMALOG® before and after 37° C. exposure for 2, 4 and 8 days. Included in this study were Malvern size distributions, reverse phase HPLC, size exclusion chromatography and FTIR analysis.

Figure 22A:
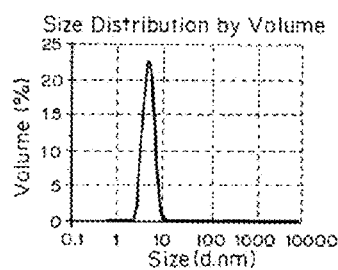
FIGS. 22A-22D are chromatograms showing the Malvern size distributions by volume (volume (%) versus particle size (d·nm)) for HUMALOG® (22A) and BIOD-250 (22C); or by intensity (intensity (%) versus particle size (d·nm)) for Humalog® (22B) and BIOD-250 (22D) during baseline conditions.
Figure 22B:
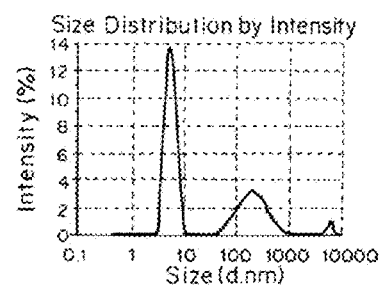
Figure 22C:
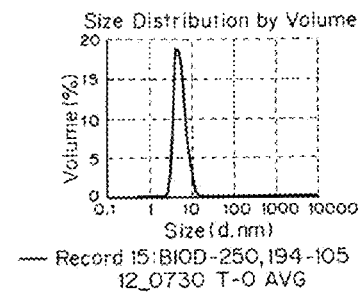
Figure 22D:
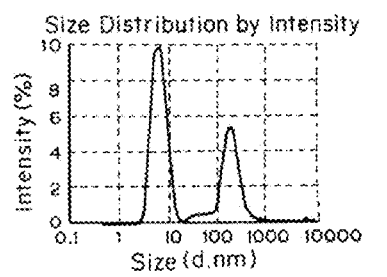

The Malvern size distributions were useful for illustrating changes in the particle size during accelerated stability conditions at 37° C. Baseline conditions for the BIOD-250 formulation and Humalog® are shown in FIGS. 22A and 22B (HUMALOG®) and 22C and 22D (BIOD-250).

The size distributions of the two formulations are very similar when BIOD-250 has been freshly made. The size distributions begin to change after two days exposure to 37° C. and after 8 days, the size distributions progressively change, showing a population of smaller and larger size insulin particles. These data are consistent with a formulation that initially starts as a hexamer, then dissociates into monomers and dimers over time. These smaller subunits then reassemble into larger insulin polymers/aggregates. With BIOD-250 hexameric degradation has only partially occurred by Day 2 and by Day 4 there is still a large amount of lispro in the hexameric form; monomerization takes place at 37° C. over a period of days to a week. In light of these data, it is important to note that even after immediate mixing of the excipients, a rapid PK is achieved (see "Just In Time" Mixing Stabilization Technology" section in Research Plan), despite the fact that much of the lispro still exists in the hexameric state. This supports the hypothesis that the rapid PK does not require monomer formation in the vial and opens up the possibility that one can slow or halt hexamer degradation in the vial without sacrificing the ultra-rapid-acting pharmacokinetic profile.

Figure 23A:
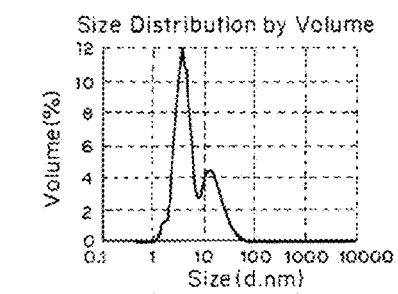
FIGS. 23A-23B are chromatograms showing the Malvern size distributions by volume (volume (%) versus particle size (d·nm)) (23A); or by intensity (intensity (%) versus particle size (d·nm)) (23B) for BIOD-250 during accelerated stability conditions at 37° C.
Figure 23B:
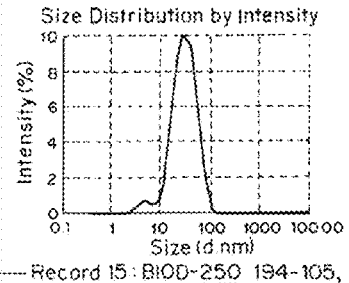

The data in FIGS. 23A and 23B show that the hexamer is dissociating over time leading to conditions which allow for the formation of higher molecular weight species. This is confirmed by the size exclusion chromatography results. Both formulations begin with a very similar size exclusion chromatography profile. However, by 8 days the high molecular weight protein has grown considerably in the BIOD-250 formulation.

Another method for characterization of the state of the insulin "in the bottle" is analytical ultracentrifugation. The following ultracentrifugation studies were conducted at the University of Connecticut analytical ultracentrifuge facility. Each sample was provided as a complete formulation with a corresponding diluent that had the exact same composition of the formulation without the insulin. The samples were analyzed neat and diluted with the diluents at 1:2, 1:6 and 1:20. Svedberg constants for HUMALOG® and BIOD-250 were determined; studies have not been carried out under accelerated conditions (i.e. exposure at 37° C.). The average S(w,20) from these experiments for undiluted Humalog® is 3.05, and for BIOD-250 is 2.4.

The results show a reduction of the BIOD-250 Svedberg constant compared to HUMALOG®, going from S(w,20) 3.05 for Humalog®, to 2.4 for BIOD-250. On dilution, the BIOD-250 formulation progresses to a population of monomeric insulin while HUMALOG® shifted only slightly towards the smaller size distribution.

This reduced S(w,20) average includes many insulin associated forms, including monomers to dodecamers (S(w,20)~4.5). Since these experiments were run with formulations which had been produced approximately one month earlier, it is not surprising that the starting population is not primarily hexameric since the Malvern data show that after production the hexamer population in BIOD-250 declines over time. On dilution, the BIOD-250 rapidly dissociates to a monomer population with a S(w,20)=1.2.

In another study using differential scanning calorimetry (DSC), there was further evidence of a mixture of insulin forms. DSC studies were conducted with BIOD-238 and BIOD-250, using HUMULIN® and HUMALOG® for comparators. Both Biodel formulations had been made up well in advance of the experiment and thus likely already had most to all of the zinc-stabilized hexamers transformed to monomers and various other oligomeric forms. The thermogram of HUMULIN® showed a single phase transition ($T_m$) at 84.7° C., which is contributed by insulin hexamers HUMALOG® showed two peaks with some extent of overlap, one at 64.8° C. ($T_m1$) and the other at 80.9° C. ($T_m2$). $T_m1$ was within the native insulin monomer and dimer (~67° C.) (phase transition range according to literature). $T_m2$ was contributed by hexamer, although the insulin lispro hexamer melting $T_m$ was lower than the human insulin hexamer observed in this study (HUMULIN®, $T_m$ 84.7° C.). The reduced hexamer $T_m$ is likely due to the modified amino acid sequence in insulin lispro.

BIOD-250 did not show the designated monomer and hexamer peaks that were seen with HUMALOG®. Instead, the thermogram of BIOD-250 had one broad phase transition peak centered at 68° C. when analyzed by a non-two state model. If the data were fitted with two non-two state model, peaks at 64.2° C. ($T_m1$) and 74.8° C. ($T_m2$) were derived. $T_m1$ was in the same range of lispro monomer/dimer observed in this study and the derived peak area of $T_m1$ in BIOD-250 was much larger than $T_m1$ in HUMALOG®. This suggests that the monomer/dimer distribution increased in the BIOD-250. The thermogram of BIOD-250, shows a single broad peak. Further modeling using two non-two state model distinguished two peaks with a $T_m1$ at 64.12° C. and $T_m2$ at 74.8° C.

A similar result was observed in BIOD-238. Deconvolution of the single transition temperature showed $T_m1$ at 74.05° C. and $T_m2$ at 63.59° C. The changes in transition temperature show an increase in the lispro monomer/dimer concentration with the addition of EDTA and citric acid to the formulation (BIOD-238 and BIOD-250). There also appears to be a mixture of insulin species, including larger molecular weight forms such as trimers, tetramers and possibly some hexamers, which are difficult to differentiate with this technique.

These techniques show that it is likely that the insulin lispro hexamer has been destabilized by the addition of EDTA and citrate to the formulation and over time (days at 37° C.) most hexamers have disappeared due to the chelation of zinc. It is noteworthy that disassociation of the hexamers prior to injection is not required in order to achieve the ultra-rapid-acting profile since the Malvern data show that that effect is not immediate but instead occurs over days at 37° C.

Since monomeric insulin is susceptible to the formation of HMWP species, it is not surprising that size exclusion chromatography results show an accelerated formation of HMWP. Both formulations begin with a very similar size exclusion chromatography profile. However, by 8 days, the high molecular weight protein has grown considerably in the BIOD-250 formulation. Destabilization of the hexamers creates an environment where monomers can combine into larger aggregates, including polymers, which is further enhanced under 37 C accelerated conditions. However, an ultra-rapid-acting PK profile is not dependent on a transition away from hexamers in the vial prior to injection.

Strategies for Retaining Insulin Hexamer in the Bottle

In comparison to hexameric forms, the native insulin monomer is a more chemically and physically labile species. A primary driver of degradation is exposure of certain hydrophobic residues, normally buried in the three-dimensional structure of the hexamer, to the surface of the insulin monomer. Hence it is a goal not to fully disassociate the hexamer and create monomeric insulin but instead create a formulation that more rapidly disassociates upon injection yet has a commercially viable stability profile.

It is well known that lispro has a significantly different dissociation process from the hexameric complex than insulin and unlike insulin, needs both phenolic ligands and zinc to form hexamers. In addition, lispro has a dimerization constant 2 to 3 orders of magnitude lower than insulin. These differences may be the reason why lispro exhibits a lower stability than RHI when formulated with the Biodel excipients.

Strategies to meet the target product profile include increase the stability of the R6 hexamer within the vial (or cartridge) and rely upon ligand disassociation after injection to enable chelation. This can be accomplished by using some combination of (i) Stronger phenolic ligand (e.g. resorcinol); (ii) stronger anionic ligand (e.g. thiocyanate); or (iii) a weaker chelator (e.g. cysteine)

It is well known that zinc is inaccessible when the hexamer is in the R6 state and there is evidence that in a T3R3 or T6 state, zinc can be chelated out of the hexamer. Since the transition across the various states (i.e. R6<->T3R3<->T6) is partly driven by the concentration and type of ligands binding to the hexamer, the rate of chelation can be limited by increasing the amount of time in the R6 state by changing ligand types and concentration. In addition, weaker chelators may not effectively capture the zinc ion when the hexamer is in a T3/R3 or T6 state.

Substitutions of Phenolic and Anionic Ligands

Further stabilization of the lispro hexamer prior to adding the Biodel ultra-rapid excipients can be a key to the long-term stability of the Drug product. The absolute need for Zn and Phenol to form the lispro hexamer in Humalog® is well understood (Birnbaum, et al; *Pharm Res.*, 14(1) 25-36 (1997)). Hexameric insulin is an allosteric protein that undergoes transitions between three general conformational states ($T_6$, $T_3R_3$, and $R_6$). Two kinds of important binding sites exist in hexamers for various allosteric ligands: (1) Two anionic binding sites which can bind single anions such as chloride, phenolate, carboxylates or thiocyanate, and (2) Six 'hydrophobic binding pockets' located on dimer-dimer interfaces in hexamers which can bind small organic ligands such as phenol. Both kinds of allosteric ligands play a central role in T<=>R transition. These allosteric states are stabilized by the binding of ligands to the phenolic pockets within the insulin molecules and by the coordination of anions to the His B10 metal sites. The phenol molecules bind to the nonpolar cavities in the interface between the dimers (A-chain residues from one dimer and the B1-B8 helical segment from the adjacent dimer). In contrast to RHI, lispro exhibits very weak hexamer association behavior in the absence of Zn. In fact, Zn alone will not form the lispro hexamer since it requires the phenolic ligands to form a phenol-stabilized T3Rf3 zinc hexamer (Betenson, D F et al; *Ann. NY Acad. Sci.*, 2011 December: 1243:E40-E54).

Resorcinol is well known to have a higher binding affinity to the lispro molecule (Ferrari, D et al; *Biopolymers*, 62(5): 249-260 (2001)). Resorcinol can be added to the formulation at a pH ranging between 6.8 to 7.8.

The insulin literature has identified the chloride anion (Cl⁻) as a hexamer stabilizing agent (Brader, et al. *Biochemistry*, 30(27):6636-45 (1991); Huus M et al. *Biochemistry*, 45(12): 4014-24 (2006); Brzovic P S et al. *Biochemistry*, 33(44): 13057-13069 (1994)). This general stabilization effect has been well studied and has its basis in the Hofmeister series that ranks the relative influence/interaction of ions on the physical behavior of aqueous colloids and proteins. For insulin, the anions bind to the Zn molecules within the interior of the hexamer. Biodel research has documented this stabilization effect of Cl⁻ anion on the Linjeta™ product.

Anions that can be used KSCN (note: SCN⁻ is only approved for intravenous use but has displayed the highest binding affinity to Zn in insulin); sodium chloride; sodium benzoate; sodium thioglyconate; monosodium glutamate; sodium glycinate; Trimethylamino oxide.

Alternative Chelators

The characterization data of formulations made from HUMALOG® with the addition of the Biodel ultra-rapid excipients formulations suggest that the use of disodium EDTA completely sequesters the Zn from within the lispro hexamer. This Zn removal leads to a higher concentration of lispro monomer and thereby reduces the overall molecular stability of the lispro/HUMALOG® drug product. The instability appears to be more pronounced at both 25° C. and 37° C. where we see a rapid increase in HMWP and related compounds indicating that we may have also changed the tertiary structure of the lispro and not just moved the equilibria towards the monomer.

EDTA is a strong chelating agent as evidenced by its stability constant (log $K_1$=16.5) with Zn (CRC Handbook of Food Additives, $2^{nd}$ ed. 1972). Biodel believes that either the use of EDTA with the most stabilized Zn/phenolic and anionic ligands lispro hexamer complex at its most stable pH or the use of weaker binding chelators with the stabilized lispro hexamer may maintain acceptable drug product solution stability alone or when combined with other stabilizing ligands or in combination with the "Just In Time" described below.

The following sequestering agents (chelators) which have lower binding affinities than EDTA can be used in the formulations disclosed herein: Nitrilotriacatic acid (NTA; log $K_1$=10.450); Cysteine (log $K_1$=9.8); Histidine (log $K_1$=6.63); Glutamic Acid (log $K_1$=5.45); Valine (log $K_1$=5.0) [Note: Citric Acid is also a chelator (log $K_1$=4.5) but is already a constituent of the Biodel ultra-rapid excipients combination.]. The prochelator chosen would be based on an analysis both of available toxicology data on the active chelator as well any published literature on the speed at which the prochelator converts to the active molecule in the presence of $H_2O_2$.

Another stabilization strategy is to add stabilizing excipients (e.g. osmolytes, surfactants, antigelling etc.) to minimize degradation regardless of the quaternary structure of the lispro. It is well known that specific routes of degradation can be slowed with specific stabilizing excipients. While on its own this may not be adequate, it is likely that leveraging one or more of these excipients could in combination with other strategies allow us to achieve the target stability profile.

Still another strategy is to use an environmental change upon injection to trigger chelation. For example, lispro could be formulated in acidic conditions (as close as possible to the isoelectric point) and a chelator (e.g. cysteine) that will chelate zinc only at physiological pH, selected. Many compounds with significant chelation activity do not chelate at pH lower than 6. Examples include histidine and cysteine (FIG. 2 in Faa, G. et al; Coordination Chemistry Reviews, Vol, 252 (2008) 1257-1269). The trade off with this approach is increased deamidation and the production of A-21 at lower pH. However, the formulation can additionally include agents that lower deamidation rates and/or the pH at which insulin and some analogs stay in solution can be increased using methods that are known in the art (pH 5 would be adequate for this approach).

Still another approach is to use a prochelator which is inactive in the vial and becomes converted to the active moiety following injection in the subcutaneous space. There has been significant research into prochelators that could be used as therapeutic agents targeted against neurodegenerative diseases (Charkoudian, L K; 2009 ProQuest, LLC, Perez, L R and Franz, K; Dalton Trans., 2010 Mar. 7 Vol. 39(9) 2177-87, Dickens, M G, et al; Chembiochem., 2010 Jan. 4; Vol. 11(1) 59-62). One example is based on salicylaldehyde isonicotinoyl hydrazone (SIH) an investigational orally effective chelator. A prochelator of SIH can be created by replacing a phenol oxygen, a key chelating atom, with a boronic acid group (Charkoudian, L K and, Franz, K J; *J. Am. Chem. Soc.*, 2006 Sep. 27 Vol. 128(38)12424-5). The protecting boronic acid group in SIH-B is cleaved when in the presence of $H_2O_2$, and is thus "activated" to produce the active chelator SIH (Wei, Y and Guo, M; *Angew Chem. Int. Ed Engl.*, 2007 Vol. 46(25) 4722-4725). Numerous compounds (ascorbic acid, xanthine, most amino acids) could be safely added to the formulation and produce H2O2 at the injection site (Chen, et al; *Proc. Natl. Acad. Sci.*, USA, 2007 May 22 Vol. 104(21) 8749-54, Lacy, F, et al; *Free Radic. Biol. Med.*, 1998 October Vol. 25(6)720-7). In addition there is a steady state production of $H_2O_2$ in plasma (Lacy, F, et al; *Free Radic. Biol. Med.*, 1998 October Vol. 25(6)720-7) which coupled with $H_2O_2$ triggered by the injection (Niethammer, P, et al; *Nature*, 18 Jun. 2009 Vol. 459 996-999) may be adequate in itself. Whether this can occur quickly enough to maintain an ultra-rapid-acting profile would have to be tested experimentally.

A further strategy is to decrease the amount of time that the destabilizing excipients are combined with the "base" lispro formulation (see Mixing Stabilization Technology below).

While degradation rates are lowest at 5° C., eliminating the 18 to 24 months of incremental degradation at 5° C. caused by the additional excipients may significantly decrease the gap between the target stability profile and the current stability profile. It is likely that utilizing this strategy alone would enable 24 months dating with a 14 to 28 days in-use label for MDI usage. This is a relatively low risk strategy and requires the design (some examples are known in the art) of primary containers (cartridge, prefilled pen, vial) which add the excipients upon first use (removal of cap from vial or first insertion of needle, first movement of plunger in cartridge). This strategy could be combined with other strategies disclosed herein.

Degradants can also be included in the formulation. There are a finite number of limiting degradants that determine the shelf life and in-use profile for insulin and insulin analogs. For a lispro-based BIOD formulation this is currently HMWP and potency. If formulated at a lower pH taking advantage of pH triggered chelation, then A-21 would likely become the limiting degradant. The specifications for HMWP for RHI are <1.7% while the same specification set by Lilly for lispro is <1.5%.

EXAMPLE 10

Optimizing Stability of Base Formulation with Regards to EDTA and Citrate Concentrations BIOD-238 and BIOD-250 are ultra-rapid-acting insulin formulations which combine the marketed product, Humalog® with Linjeta™ excipients.

Figure 24:
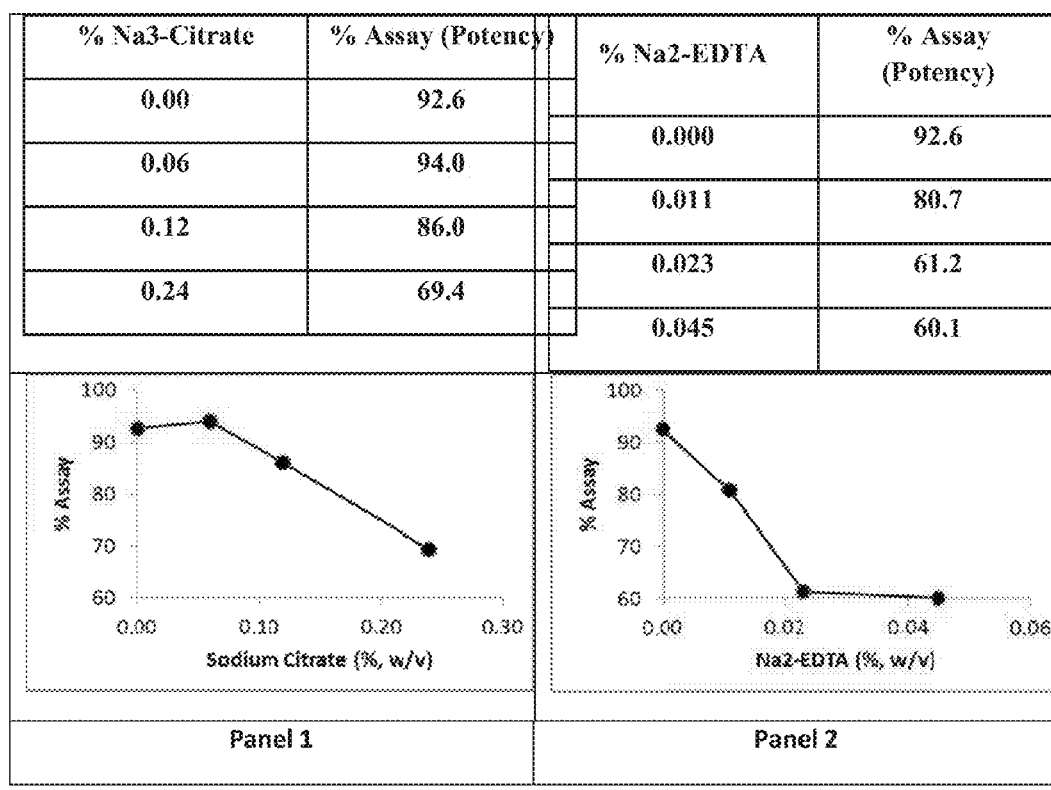
FIG. 24 is a graph of the dose-dependent effects of sodium citrate (Panel 1) and disodium EDTA (Panel 2) on reducing the stability of lispro formulations under accelerated testing conditions.
Figure 25:
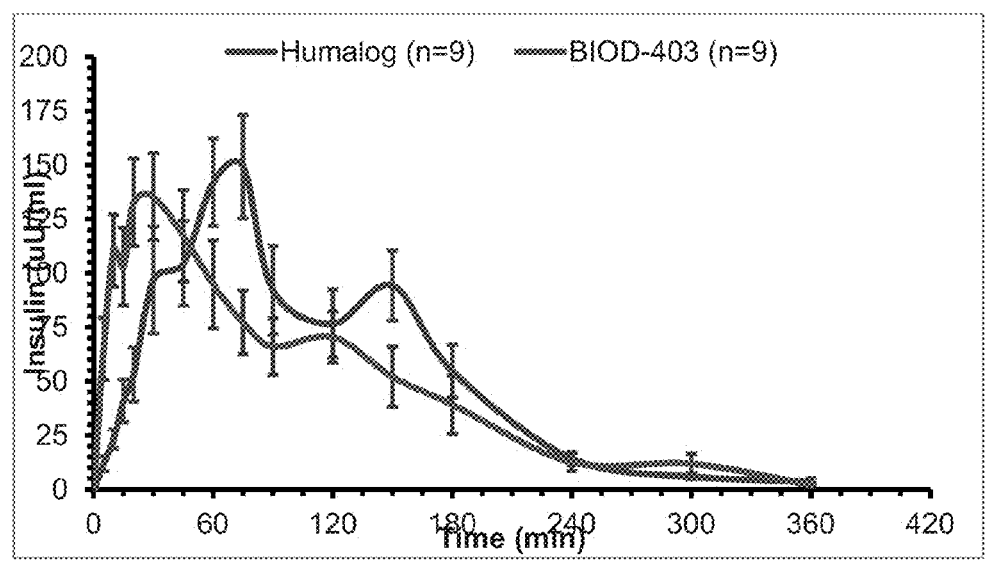
FIG. 25 shows the mean baseline subtracted insulin lispro versus time of Humalog® versus BIOD-403, 0-360 minutes post dose.

Commercial Humalog® was dialyzed to remove formulation components other than lispro and m-cresol. A formulation matrix was designed to vary the composition and concentration of the key LINJETA™ excipients. The test articles were screened using accelerated conditions. The samples were held at 50° C. for 48 hours followed by HPLC analysis. The "% Assay" was determined by comparing the insulin analog concentration after 'stress' to the samples and the values are expressed as a percentage of the t=0 value. The study demonstrated that an additional reduction in citrate and EDTA concentration was beneficial to formulation stability (FIGS. 24A and B).

Reductions in the $MgSO_4$ concentration had no significant impact on formulation stability while increasing the zinc content in the formulation had a positive effect on both potency and HMWP content (Table 28). The initial Zn concentration after dialysis was not measured.

TABLE 28

Dose-dependent effects of zinc oxide on increasing stability of lispro formulation tested under accelerated conditions.

| Zn (%) | % HMWP | % Assay (potency) |
|---|---|---|
| 0.002 | 19.6 | 61.3 |
| 0.004 | 1.8 | 94.9 |
| 0.008 | 1.5 | 95.5 |
| 0.010 | 0.5 | 98.6 |

Additional modifications in one or more of the formulation components can have a beneficial effect on stability. Further reductions in EDTA and citrate as well as a nominal increase in the zinc content in a matrix design based on the prototype formulation BIOD-250 (Table 26) can be used to increase stability.

TABLE 29

Summary of initial matrix design to evaluate effects of EDTA, citrate and zinc

| Formulation | EDTA (mg/mL) | Citrate (mg/mL) | Zn Oxide (mg/mL) |
|---|---|---|---|
| 1 | 0.45 | 1.6 | 0.0197 |
| 2 | 0.45 | 2.4 | 0.0197 |
| 3 | 0.45 | 2.4 | — |
| 4 | 0.225 | 2.4 | 0.0197 |
| 5 | 0.1125 | 2.4 | 0.0197 |
| 6 | 0.225 | 2.4 | 0.0394 |
| 7 | 0.1125 | 1.2 | 0.0197 |
| 8 | 0.1125 | 0.6 | 0.0197 |
| 9 | 0.225 | 1.2 | 0.0197 |
| 10 | 0.45 | 2.4 | 0.0394 |

Solution Polymerization Control

The characterization data has indicated that BIOD-250 and BIOD-238 formed higher order aggregates at 25° C. and 37° C. as compared to HUMALOG®. The polymerized insulin seems to be formed via covalent bonding of the monomers at the accelerated temperatures. The insulin covalent aggregation would then be dependent upon the initial population of intermediates and the amount of free monomer in solution. It is believed that if the hexamer is stabilized (reducing the amount of monomer in solution), the rate of HMWP production in the drug product would be altered. Additionally, it is also known that certain osmolytes have a stabilizing effect on insulin by inhibiting aggregation (steric interference) and tertiary structure maintenance (Preferential exclusion effect arising from increased non-attractions between the osmolyte (i.e. polyols) and the protein) (Xie, G. et al., Protein Sci. 6, 211 1997). Additional stabilization routes to reduce HMWP formation in the optimized formulation include steric interference compounds, alternative buffer combinations, and polyols.

Steric Interference Compounds

The addition of a steric interference excipient potentially will make the active groups on or the intermediate structures of the peptide not readily accessible to each other. A successful inhibitor will produce entropically unfavorable interpenetration, and inhibit bonding. Trimethylamine N-oxide (TMAO) is one possible candidate. This molecule has demonstrated the ability to refold protein from an unfolded state, and more importantly to retain the preferential confirmations of peptides. The primary mode of TMAO action appears to be an increase in interaction with water and a decrease in amide interactions (Olin Zou et al., Pub. Med. Molecular Mechanism of Stabilization 2002 p 1192-1200). A second excipient is a small heat shock protein, alpha crystalline, which may provide a "scaffolding" interaction on proteins to help maintain their tertiary structure (G. Maulucci et al., Thermal Structure Transition; The Crystalin, Pub. Med. 9426193). The third group is amphiphilic surfactants which are all expected to operate via a similar site-interfering mechanism (one end of the steric interference compound is thought to anchor toward the peptide molecule, and the other end is extended into the surrounding solvent or may locally immobilize the tertiary structure through solvent interactions. Examples include Poloxamer 407 (Pluronic F127) (J H Atwood et al., Micellan Properties; Intervention Journal of Pharmaceutics 9/1986/p 25-33) and Tween 80.

Physical Aggregation/Fibril Formation: The physical aggregation of lispro seems to be formed via the partial unfolding of insulin lispro monomers, which then act as a "seed". The unfolded monomer assembles into filaments, and continues growing into fibrils. Some "seeds" may form in solution, by Van der Waals interaction despite zeta repulsion, but the most efficient formation condition prevails at the solution, gas interface, where peptide molecules tend to orient themselves with their hydrophobic regions above the surface, to minimize free energy. The exposed "tails" may freely interact, forming Van der Waals bonds, and providing polymerization "seeds", with improved efficiency.

A possible strategy for reducing this effect would be a surface film of an appropriate surfactant (as outlined above) or a non-miscible lipid, which would reduce the accessibility of "tail"/"tail" interactions at the interface. Lipid content would be kept very low, far below the critical micelle concentration, to prevent lipid/lipid interactions from competing with lipid/peptide interactions. As a probe only, a low viscosity member of the Dow Chemical 200 silicone family could be used. This would insure that only hydrophobic physical processes occur, with no chemical interaction.

A second approach is through electrostatic repulsion. Intermolecular forces in solution are a balance between electrostatic repulsion, caused by the surface boundary layer, and the Van der Waals attraction. For the solution to remain stable, the boundary layer repulsion, usually summed up as the zeta potential, must be larger than the Van der Waals forces. This is generally not true at all distances. Therefore repulsion must act at several boundary layer dimensions, to be effective.

A glycine buffer can be used to improve this balance. Glycine is the smallest of the endogenous amino acids, and is its own isomer. It can bond to either hydrophobic or hydrophilic regions, and may influence polymerization reduction through two effects. First it will tend to "smooth out" the shape of the boundary layer (Debye surface), by reducing the local gradients, and second by reducing the net Van der Waals attraction between molecules.

While degradation rates are lowest at 5° C., eliminating the 18 to 24 months of incremental degradation at 5° C. caused by the ultra-rapid-acting insulin excipients may significantly decrease the gap between the target stability profile and the current stability profile.

BIOD-403 represents a vial of Humalog® to which the BIOD-250 excipients were added just prior to subcutaneous administration in diabetic swine. BIOD-403 has a "rapid on/rapid off" profile which is comparable to BIOD-250 and faster than HUMALOG®.

Modifications and variations will be apparent to those skilled in the art and are intended to come within the scope of the invention.

We claim:

1. An injectable insulin formulation comprising
   (a) monomeric insulin, dimeric insulin, or both,
   (b) an effective amount of a dissolution/stabilizing agent to stabilize the monomeric and dimeric insulin,
   (c) an effective amount of a chelator to chelate the zinc in the insulin, and
   (d) an effective amount of one or more magnesium compounds to decrease injection site pain, compared to the same formulation with sodium EDTA that does not include the one or more magnesium compounds, and
   wherein the formulation does not significantly alter the rate of uptake of the insulin, compared to the same formulation with sodium EDTA, which does not include the one or more magnesium compounds.

2. The formulation of claim 1 wherein the insulin is human recombinant insulin.

3. The formulation claim 1 where the insulin is an insulin analog.

4. The formulation of claim 1 wherein the insulin concentration is 100, 200, 400 or 500 U/mL.

5. The formulation of claim 1, wherein the one or more magnesium compounds are selected from the group consisting of inorganic magnesium salts, organic magnesium salts, and combinations thereof.

6. The formulation of claim 5, wherein the inorganic magnesium salts are selected from the group consisting of magnesium hydroxide ($Mg(OH)_2$), magnesium sulfate ($Mg(SO_4)_2$), magnesium pyrophosphate, magnesium sulfate heptahydrate, magnesium oxide ($MgO_2$), and combinations thereof.

7. The formulation of claim 5, wherein the organic magnesium salts are selected from the group consisting of magnesium EDTA, magnesium lactate, magnesium acetate, magnesium carbonate ($Mg(CO_3)_2$), magnesium citrate, and magnesium gluconate.

8. The formulation of claim 1, wherein the one or more magnesium compounds are $Mg(OH)_2$, $MgSO_4$, magnesium EDTA, or combinations thereof.

9. The formulation of claim 1, wherein the concentration of the one or magnesium compounds is between about 0.1 and about 10 mg/ml.

10. The formulation of claim 1, wherein the formulation contains about 0.2-0.3 mg/ml $Mg(OH)_2$, about 1.7-2.0 magnesium EDTA, about 0.4-0.5 magnesium sulfate, or combinations thereof.

11. The formulation of claim 1 wherein the dissolution/stabilization agent is selected from the group consisting of acetic acid, ascorbic acid, citric acid, glutamic, succinic, aspartic, maleic, fumaric, adipic acid, and salts thereof.

12. The formulation of claim 1 wherein the dissolution/stabilization agent forms citric ions and the pH is about 7.

13. The formulation of claim 11 wherein the dissolution/stabilization agent is citric acid or sodium citrate.

14. The formulation of claim 11 wherein the dissolution/stabilization agent is citric acid or sodium citrate in a range between $2.0 \times 10^{-4}$ M and $4.5 \times 10^{-3}$ M.

15. The formulation of claim 1 wherein the dissolution/stabilization agent is citric acid or sodium citrate in a range between $7 \times 10^{-3}$ M and $2 \times 10^{\times 2}$ M.

16. The formulation of claim 1 wherein the dissolution/stabilization agent is citric acid or sodium citrate at about $9.37 \times 10^{-3}$ M or about $1.4 \times 10^{-2}$ M.

17. The formulation of claim 1 further comprising calcium chloride.

18. The formulation of claim 1 further comprising glycerine and m-cresol.

19. The formulation of claim 1, wherein the chelator is sodium EDTA.

20. The formulation of claim 5, wherein the inorganic magnesium salts are magnesium halides, selected from the group consisting of magnesium chloride ($MgCl_2$), magnesium bromide ($MgBr_2$), magnesium iodide ($MgI_2$) and combinations thereof.

21. The formulation of claim 5, wherein the organic magnesium salts are magnesium amino acid chelates.

22. The formulation of claim 21, wherein the magnesium amino acid chelate is magnesium aspartate.

23. The formulation of claim 9, wherein the concentration of the one or magnesium compounds is between about 0.1 and about 5 mg/ml, between about 0.1 and about 2 mg/ml, or between about 0.2 and about 2 mg/ml.

* * * * *